US010172831B2

(12) United States Patent
Taylor et al.

(10) Patent No.: US 10,172,831 B2
(45) Date of Patent: Jan. 8, 2019

(54) CATALYTIC SCAVENGERS OF ORGANOPHOSPHATES TO POTENTIATE BUTYRYLCHOLINESTERASE (HBCHE) AS A CATALYTIC BIOSCAVENGER AND METHODS FOR MAKING AND USING THEM

(71) Applicants: THE REGENTS OF THE UNIVERSITY OF CALIFORNIA, Oakland, CA (US); THE SCRIPPS RESEARCH INSTITUTE, La Jolla, CA (US)

(72) Inventors: Palmer Taylor, La Jolla, CA (US); Zoran Radic, La Jolla, CA (US); Valery Fokin, Lo Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/028,669

(22) PCT Filed: Oct. 15, 2014

(86) PCT No.: PCT/US2014/060666
§ 371 (c)(1),
(2) Date: Apr. 11, 2016

(87) PCT Pub. No.: WO2015/057822
PCT Pub. Date: Apr. 23, 2015

(65) Prior Publication Data
US 2016/0256438 A1    Sep. 8, 2016

Related U.S. Application Data

(60) Provisional application No. 61/891,315, filed on Oct. 15, 2013.

(51) Int. Cl.
| | | |
|---|---|---|
| *A61K 31/5377* | (2006.01) | |
| *A61K 31/4164* | (2006.01) | |
| *A61K 31/4439* | (2006.01) | |
| *A61K 45/06* | (2006.01) | |
| *A61K 38/46* | (2006.01) | |

(52) U.S. Cl.
CPC ...... *A61K 31/4164* (2013.01); *A61K 31/4439* (2013.01); *A61K 31/5377* (2013.01); *A61K 38/465* (2013.01); *A61K 45/06* (2013.01); *C12Y 301/01008* (2013.01)

(58) Field of Classification Search
CPC ............ A61K 31/5377; A61K 31/4164; A61K 31/4439
See application file for complete search history.

(56) References Cited

FOREIGN PATENT DOCUMENTS

WO    2012083261 A1    6/2012

OTHER PUBLICATIONS

Sit et al, Journal of Medicinal Chemistry (2014), 57(4), 1378-1389.*
Young, International Search Report for PCT/US2014/060666, dated Dec. 19, 2014.
Sit et al, "New Structural Scaffolds for Centrally Acting Oxime Reactivators of Phosphylated Cholinesterases," The Journal of Biological Chemistry, 2011, v 286, n. 22, p. 19422-19430.
Young, Written Opinion of the International Searching Authority for PCT/US2014/060666, dated Dec. 19, 2014.
Cochran, et al., "Oxime-assisted acetylcholinesterase catalytic scavengers of organophosphates that resist aging.", J Biol Chem. 286(2011) 29718-29724. (AChE based aging resistant catalytic bioscavenger).
Mazor, et al., "Aging resistant organophosphate bioscavenger based on Phe338Ala human acetylcholinesterase", Mol. Pharmacol. 74 (2008) 755-763. (AChE based aging resistant catalytic bioscavenger).
Lenz, et al., "Reactivation kinetics of a homologous series of bispyridinium bis-oximes with nerve agent-inhibited human acetylcholinesterase", Arch Toxicol. Mar. 22, 2012. [Epub ahead of print] (Catalytic bioscavengers and reactivators of Tabun inhibited human AChE).
Worek, et al., "Reactivation kinetics of a homologous series of bispyridinium bis-oximes with nerve agent-inhibited human acetylcholinesterase", Arch Toxicol. Mar. 22, 2012. [Epub ahead of print] (Catalytic bioscavengers and reactivators of Tabun inhibited human AChE).
Radić, et al., "Catalytic detoxification of nerve agent and pesticide organophosphates by butyrylcholinesterase assisted with non-pyridinium oximes", Biochem J. 450 (2013) 231-242.

* cited by examiner

*Primary Examiner* — Rebecca L Anderson
(74) *Attorney, Agent, or Firm* — Greer, Burns & Crain, LTD.; Gregory P. Einhorn

(57) ABSTRACT

Provided are N-alkyl imidazole 2-aldoximes, including cationic imidazolium and uncharged tertiary imidazole aldoximes, and compositions and methods for making and using them, including methods for reactivating human butyrylcholinesterase (hBChE) or acetylcholinesterase (hAChE) inhibited by organophosphate (OP). By administration of a composition of the invention, the inactive or conjugated hBChE-OP or hAChE-OP is reactivated and the catalytic cycle of turnover and inactivation of the OP is completed; and in alternative embodiments, secondary mechanisms of reversible protection of hBChE and hAChE from irreversible inactivation by OPs and reactivation of tissue AChE also contribute to overall efficacy.

16 Claims, 8 Drawing Sheets

Fig. 2

Table 1

| Oxime | | $k_{obs}$ (min⁻¹) | | | | |
|---|---|---|---|---|---|---|
| | | Norm. Avrg | POX | Sarin | CS | VX |
| RS-115C | | 75 % | 0.029 | 0.250 | 0.590 | 0.370 |
| RS-115B | | 110 % | 0.023 | 0.680 | 0.480 | 0.400 |
| RS-115A | | 89 % | 0.054 | 0.220 | 0.650 | 0.480 |
| RS-113B | | 160 % | 0.190 | 0.120 | 0.440 | 1.200 |
| RS-113A | | 110 % | 0.085 | 0.180 | 0.650 | 0.860 |
| RS2-37C | | 53 % | 0.0084 | 0.089 | 1.030 | 0.0280 |

Fig. 3

Table 2.

| Oxime | | $k_{obs}$ (min$^{-1}$) | | | | |
|---|---|---|---|---|---|---|
| | | Norm. Avrg | POX | Sarin | CS | VX |
| RS2-33A | | 440 % | 0.37 | 0.75 | 6.0 | 1.2 |
| RS2-33B | | 400 % | 0.86 | 0.31 | 1.1 | 3.0 |
| RS-113B | | 130 % | 0.19 | 0.12 | 0.44 | 1.2 |
| RS2-33C | | 76 % | 0.15 | 0.15 | 0.12 | 0.36 |
| RS2-37B | | 76 % | 0.049 | 0.35 | 0.11 | 0.10 |
| RS2-38D | | 57 % | 0.013 | 0.033 | 1.6 | 0.018 |
| RS2-95C | | 38 % | 0.017 | 0.057 | 0.65 | 0.10 |
| RS2-167B | | 24 % | 0.013 | 0.076 | 0.21 | 0.053 |
| RS2-200D | | 20 % | 0.021 | 0.017 | 0.30 | 0.079 |
| RS-136A | | 17 % | 0.016 | 0.032 | 0.12 | 0.095 |
| RS-138B | | 11 % | 0.017 | 0.034 | 0.023 | 0.023 |
| RS2-170B | | 8 % | 0.0030 | 0.016 | 0.095 | 0.030 |
| RS-92B | | 3 % | 0.0084 | 0.0038 | 0.011 | 0.015 |
| 2PAM | | 140 % | 0.050 | 0.65 | 0.29 | 0.25 |

Fig. 4

Table 3.

| Oxime | | $k_{obs}$ (min$^{-1}$) | | | | |
|---|---|---|---|---|---|---|
| | | Norm. Avrg | POX | Sarin | CS | VX |
| 2PAM | | 73 % | 0.050 | 0.65 | 0.29 | 0.25 |
| TAB2OH | | 60 % | 0.17 | 0.087 | 1.6 | 0.62 |
| RS2-86B | | 45 % | 0.017 | 0.18 | 2.5 | 0.096 |
| RS2-140A | | 12 % | 0.0049 | 0.078 | 0.24 | 0.059 |
| RS2-153A | | 81 % | 0.032 | 0.23 | 5.7 | 0.084 |
| RS2-33A | | 200 % | 0.37 | 0.75 | 6.0 | 1.2 |
| RS2-33B | | 220 % | 0.86 | 0.31 | 1.1 | 3.0 |
| RS2-33C | | 41 % | 0.15 | 0.15 | 0.12 | 0.36 |

Fig. 4 (cont.)

| Oximes | potential |
|---|---|
| 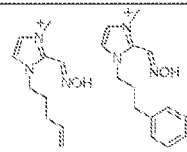<br>RS2-86B  RS2-153A | hBChE and cationic nucleophilic oxime reactivators RS2-86B and RS2-153A (or their analogues). |
| 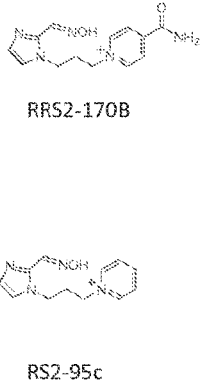<br>RRS2-170B<br><br>RS2-95c | hAChE double mutants (Y337A/F338A) and RS2-170B, RS2-95c (or their analogues).<br><br>The Y337A mutation is introduced into hAChE to confer greater resistance to permanent catalytic incapacitation by dealkylation (aging) upon covalent OP inhibition; and the F338A mutation increases the rate that OP-inhibited AChE is reactivated by the RS2-170B or RS2-95c oxime reactivators. The RS2-170B or RS2-95c oxime reactivators also assist in catalyzing the hydrolysis and

Fig. 5

Table 4.

| Oxime | | Norm. Avrg | $K_{obs}$ (min$^{-1}$) | | | |
|---|---|---|---|---|---|---|
| | | | POX | Sarin | CS | VX |
| 2PAM | (structure) | | 0.20 | 0.73 | 0.067 | 0.48 |
| TAB2OH | (structure) | | 0.025 | 0.022 | 0.0080 | 0.068 |
| RS2-86B | (structure) | 180 | > 0.001 | 0.11 | 0.073 | 0.11 |
| RS2-140A | (structure) | 110 | > 0.001 | 0.057 | 0.022 | 0.099 |
| RS2-153A | (structure) | 150 | > 0.001 | 0.11 | 0.076 | 0.037 |
| RS2-33A | (structure) | 68 | > 0.001 | 0.019 | 0.026 | 0.035 |
| RS2-33B | (structure) | 40 | > 0.001 | 0.0074 | 0.0047 | 0.019 |
| RS2-33C | (structure) | 54 | > 0.001 | 0.012 | 0.012 | 0.034 |

Fig. 6

| oxime | OP | OP-hBChE $k_2$ (min⁻¹) | $K_{ox}$ (mM) | $k_r$ (M⁻¹min⁻¹) | OP-hAChE $k_2$ (min⁻¹) | $K_{ox}$ (mM) | $k_r$ (M⁻¹min⁻¹) | $LD_{50}$ (mg/kg) | PI (therapy) |
|---|---|---|---|---|---|---|---|---|---|
| RS2-33A (3) | VX | 1.5 | 0.18 | 8 300 | 0.065 | 0.59 | 110 | 290 | 6.3 |
| | sarin | 1.3 | 0.48 | 2 700 | 0.027 | 0.29 | 93 | | |
| | cyclosarin | 7.5 | 0.17 | 44 000 | 0.033 | 0.18 | 180 | | |
| | DDVP | 0.14 | 1.9 | 74 | 0.73 | 3.0 | 250 | | |
| | paraoxon | 0.39 | 0.042 | 9 300 | - | - | ~0 | | |
| RS2-86B (12) | VX | 0.13 | 0.24 | 540 | 0.11 | 0.029 | 3600 | 89 | 7.9 |
| | sarin | 0.26 | 0.29 | 900 | 0.12 | 0.060 | 2000 | | |
| | cyclosarin | 4.6 | 0.56 | 8 200 | 0.15 | 0.70 | 220 | | |
| | DDVP | 0.040 | 0.014 | 2 900 | - | - | ~0 | | |
| | paraoxon | 0.026 | 0.36 | 72 | - | - | ~0 | | |
| RS2-33C (5) | VX | 0.37 | 0.015 | 25 000 | 0.067 | 0.66 | 102 | n.d. | n.d. |
| | sarin | 0.15 | 0.020 | 7 500 | 0.014 | 0.11 | 130 | | |
| | cyclosarin | 0.29 | 0.94 | 310 | 0.013 | 0.079 | 170 | | |
| | DDVP | 0.080 | 0.15 | 530 | 0.24 | 1.6 | 150 | | |
| | paraoxon | 0.18 | 0.02 | 9 000 | - | - | ~0 | | |
| RS2-153A (13) | VX | 0.050 | 0.020 | 2 500 | 0.056 | 0.021 | 2700 | 140 | 2.3 |
| | sarin | 0.18 | 0.048 | 3 800 | 0.15 | 0.073 | 2000 | | |
| | cyclosarin | 5.9 | 0.029 | 210 000 | 0.16 | 0.74 | 220 | | |
| | DDVP | 0.034 | 0.011 | 3 400 | - | - | ~0 | | |
| | paraoxon | 0.050 | 0.38 | 130 | - | - | ~0 | | |
| RS2-33B (4) | VX | 3.2 | 0.030 | 110 000 | 0.038 | 0.69 | 55 | ~500 | 3.0 |
| | sarin | 0.38 | 0.15 | 2 500 | 0.0077 | 0.030 | 260 | | |
| | cyclosarin | 1.3 | 0.059 | 21 000 | 0.0090 | 0.62 | 15 | | |
| | DDVP | 0.18 | 0.46 | 390 | - | - | 160 | | |
| | paraoxon | 0.87 | 0.011 | 79 000 | - | - | ~0 | | |
| RS2-140A (14) | VX | 0.071 | 0.14 | 510 | 0.12 | 0.14 | 860 | 87 | 25 |
| | sarin | 0.11 | 0.27 | 410 | 0.076 | 0.23 | 330 | | |
| | cyclosarin | 0.47 | 0.64 | 730 | 0.043 | 0.65 | 66 | | |
| | DDVP | 0.050 | 0.040 | 1 300 | 0.080 | 0.12 | 650 | | |
| | paraoxon | 0.0053 | 0.053 | 100 | - | - | ~0 | | |
| TAB2OH | VX | 2.0 | 1.5 | 1 300 | 2.4 | 23 | 100 | 100 | 5 |
| | sarin | 0.19 | 0.79 | 250 | 0.92 | 27 | 34 | | |
| | cyclosarin | 3.9 | 1.0 | 3 700 | 0.44 | 36 | 12 | | |
| | DDVP | 0.30 | 2.6 | 120 | 1.1 | 88 | 13 | | |
| | paraoxon | 0.34 | 0.71 | 480 | 0.47 | 12 | 41 | | |

CATALYTIC SCAVENGERS OF ORGANOPHOSPHATES TO POTENTIATE BUTYRYLCHOLINESTERASE (HBCHE) AS A CATALYTIC BIOSCAVENGER AND METHODS FOR MAKING AND USING THEM

RELATED APPLICATIONS

This application is a national phase application claiming benefit of priority under 35 U.S.C. § 371 to International (PCT) Patent Application serial number PCT/US2014/060666, filed Oct. 15, 2014, which claims the benefit of priority to U.S. Provisional Patent Application Serial No. (USSN) 61/891,315, filed Oct. 15, 2013. The aforementioned applications are expressly incorporated herein by reference in their entirety and for all purposes.

GOVERNMENT RIGHTS

This invention was made with government support under grants U01-NS058046, and R21-NS072086, both awarded by the National Institutes of Health (NIH). The government has certain rights in the invention.

TECHNICAL FIELD

This invention generally relates to the chemistry and mechanism of action of agents that assist in the detoxification of organophosphates (OPs) in the body. In particular, in alternative embodiments, the invention provides N-alkyl imidazole 2-aldoximes, including cationic imidazolium and uncharged tertiary imidazole aldoximes, and compositions and methods for making and using them, including methods for reactivating human butyrylcholinesterase (hBChE) or acetylcholinesterase (hAChE) inhibited by organophosphate (OP). By administration of a composition of the invention, the inactive or conjugated hBChE-OP or hAChE-OP is reactivated and the catalytic cycle of turnover and inactivation of the OP is completed; and in alternative embodiments, secondary mechanisms of reversible protection of hBChE and hAChE from irreversible inactivation by OPs and reactivation of tissue AChE also contribute to overall efficacy. In alternative embodiments, the invention provides methods comprising use of and compositions comprising: cationic and uncharged, imidazole based nucleophilic antidotes, including uncharged N-alkyl imidazole 2-aldoximes, and quaternary charged imidazolium 2-aldoximes. In alternative embodiments, these compositions of the invention are catalytic bioscavengers of OPs and enhance endogenous BChE catalysis; and in alternative embodiments are administered with BChE, e.g., systemically, topically or by inhalation, to enhance BChE catalysis of the parent OP.

BACKGROUND

BChE is currently used as stoichiometric OP bioscavenger. Due to the approximately 500-fold larger molecular mass of BChE molecules compared to nerve agent OP molecules, very large amounts of highly purified BChE protein are required for effective protection resulting in prohibitively high costs of treatment, thus restricting its application to very small number of exposed individuals.

Currently, the only approved therapies to treat OP poisoning in humans are intramuscular (IM) injections of pyridinium aldoximes, 2PAM, HI6, MMB4 or similar combined with atropine and an anticonvulsant or intravenous injection of a highly purified human butyrylcholinesterase (hBChE).

Pyridinium aldoxime therapy is directed towards nucleophilic reactivation of acetylcholinesterase (AChE) covalently inhibited by OPs to restore catalytic hydrolysis of neurotransmitter acetylcholine (ACh) and aided by protection of muscarinic ACh receptors from excess ACh by atropine. Antidotal reactivation by pyridinium aldoximes has to be initiated by intramuscular (IM) or intravenous (IV) administration, and lasts for relatively short times (e.g., 0.5 to 1 hour). Due to re-inhibition of reactivated AChE by excess lipophilic OPs that remain in the body for longer time than oximes, antidotal therapy, though inexpensive, is not effective in exposure to large OP doses and has to be repeatedly administered.

Intravenous (IV) injection of purified hBChE can covalently conjugate OP molecules that enter the circulation, thus protecting endogenous AChE in target tissues from OP inhibition. Covalent OP-hBChE conjugates are very stable and one catalytic monomer of administered hBChE can effectively destroy only one, about a 500-fold smaller molecule, of OP, thus requiring administration of a large mass of purified hBChE protein for efficient protection. While proven effective, this "stoichiometric bioscavenger" hBChE therapy is prohibitively costly and administration of large amounts of protein by injection is sufficiently impractical for expeditious treatment of large OP exposed populations in field settings.

SUMMARY

In alternative embodiments, the invention provides compounds, compositions or formulations comprising:
(a) a compound having a formula selected from the group consisting of:

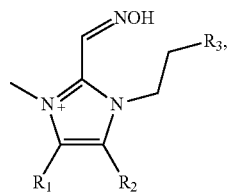

Formula I

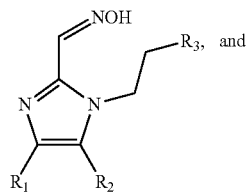

Formula II, and

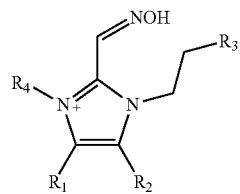

Formula III wherein:
$R_1$ is selected from the group consisting of: —H, —OH, -alkyl, -aryl, —O-alkyl, and —O-aryl (wherein optionally the alkyl is selected from the group consisting of: -methyl, -ethyl, -propyl, -butyl, -i-propyl, and -i-butyl) (wherein optionally the aryl is selected from the group consisting of: -phenyl, -naphthyl, -thienyl, and -indolyl);

R₂ is selected from the group consisting of: —H, —OH, -alkyl, -aryl, —O-alkyl, and —O-aryl (wherein optionally the alkyl is selected from the group consisting of: -methyl, -ethyl, -propyl, -butyl, -i-propyl, and -i-butyl) (wherein optionally the aryl is selected from the group consisting of: -phenyl, -naphthyl, -thienyl, and -indolyl);

R₃ is selected from the group consisting of:

H, alkyl (wherein optionally the alkyl is selected from the group consisting of: -methyl, -ethyl, -propyl, -butyl, -i-propyl, and -i-butyl), cycloalkyl (wherein optionally the cycloalkyl is selected from the group consisting of: -cyclopropyl, -cyclobutyl, -cyclopentyl, -cyclohexyl, -cycloheptyl, and -cyclooctyl), aryl (wherein optionally the aryl is selected from the group consisting of: -phenyl, -naphthyl, -thienyl, and -indolyl), a saturated heterocyclic and/or a nonsaturated heterocyclic (wherein optionally the saturated heterocyclic and/or a nonsaturated heterocyclic is selected from the group consisting of: -aziridine, -oxirane-thiirane, -azirine, -oxirene, -thiirene, -azetidine, -oxetane, -thietane, -azete, -oxete, -thiete, -pyrrolidine, -oxolane, -thiolane, -pyrrole, -furan, -thiophene, -piperidine, -oxane, -thiane, -pyridine, -pyran, -thiopyran, -azepane, -oxepane, -thiepane, -azepine, -oxepine, -thiepine, -azocane, and -azocine), a bridged compound (wherein optionally the bridged compound is selected from the group consisting of: -adamantanes, -amantadines, -biperidenes, -memantines, -methenamines, -rimantadines, -norbornanes, and -triazoles), and a structure selected from the group consisting of:

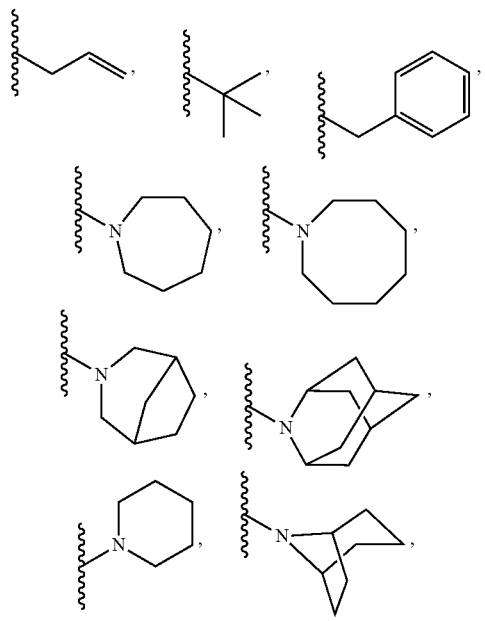

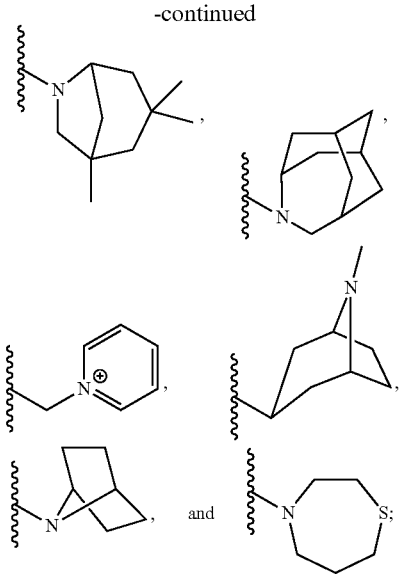

and

R₄ is selected from the group consisting of: —H, —OH, -alkyl, -aryl, —O-alkyl, and —O-aryl (wherein optionally the alkyl is selected from the group consisting of: -methyl, -ethyl, -propyl, -butyl, -i-propyl, and -i-butyl) (wherein optionally the aryl is selected from the group consisting of: -phenyl, -naphthyl, -thienyl, and -indolyl);

(b) an N-alkyl imidazole 2-aldoxime capable of forming a zwitterion, or, a quaternary N-alkyl methyl imidazolium 2-aldoxime;

(c) an analog of any of (a) or (b), wherein optionally the analog comprises a structure of any of (a) or (b) wherein another heterocycle replaces the imidazole or imidazolium ring and/or a different alkyl substitution is made at the 1 and 3 nitrogen positions, or a substitution is made at the 4 and 5 positions of the imidazole or imidazolium rings;

(d) a bioisostere of any of (a), (b) or (c), wherein optionally one or more hydrogen atom(s) are replaced with one or more fluorine atom(s);

(e) a salt of, or a pharmaceutically acceptable salt of, any of (a), (b) or (c), wherein optionally the salt comprises a mesylate or a methane sulfonate salt; or (f) any combination thereof.

In alternative embodiments, compounds, compositions or formulations of the invention have a structure or formula selected from the group consisting of:

(a) a structure or formula selected from the group consisting of:

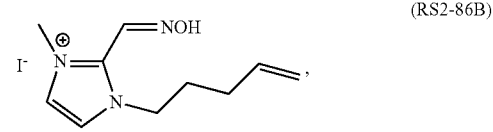
(RS2-86B)

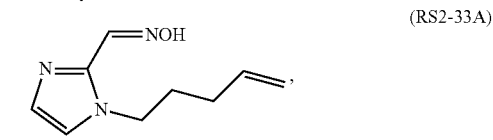
(RS2-33A)

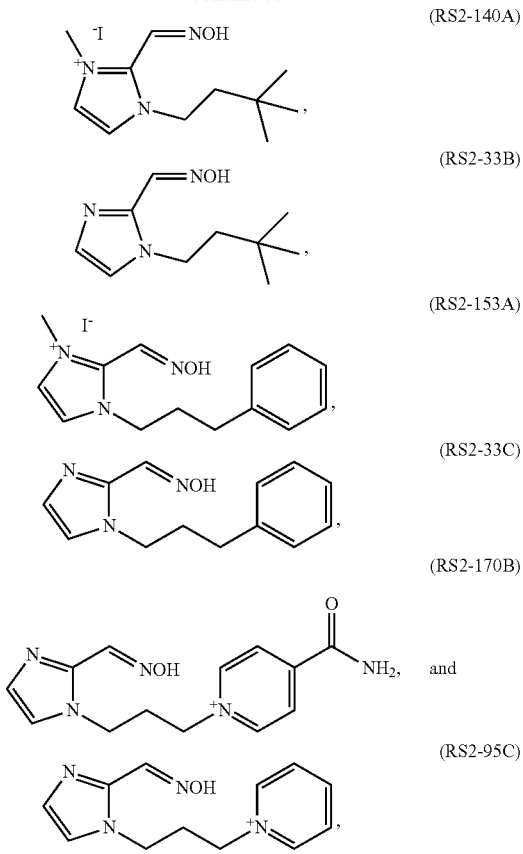

and (b) a structure or formula of (a), wherein the anion I⁻ is replaced by another anion or a negatively charged molecule or moiety.

In alternative embodiments, compounds, compositions or formulations of the invention are oximes that have a high affinity or low apparent dissociation constant (low $K_{ox}$ in the vicinity of 0.01 and 0.03 mM, see FIG. 6.

In alternative embodiments, compounds, compositions or formulations of the invention are formulated for administration in vivo; or for enteral or parenteral administration, or for ophthalmic, topical, oral, intravenous (IV), intramuscular (IM), intrathecal, subcutaneous (SC), intracerebral, epidural, intracranial or rectal administration, or by inhalation.

In alternative embodiments, compounds, compositions or formulations of the invention are formulated as: a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), a thin-film or dissolving film, or an implant.

In alternative embodiments, compounds, compositions or formulations of the invention, or pharmaceutical compositions or formulations of the invention, further comprise a pharmaceutically acceptable excipient.

In alternative embodiments, compounds, compositions or formulations of the invention, or pharmaceutical compositions or formulations of the invention, further comprise: (a) a butyrylcholinesterase (BChE), wherein optionally the BChE comprises a human butyrylcholinesterase (hBChE), or optionally the butyrylcholinesterase (BChE) comprise a recombinant BChE (rBChE) or a peptidomimetic BChE; or, (b) one or more additional drugs or formulations, wherein optionally the additional drug or formulation comprises a muscarinic acetylcholine receptor antagonist (a muscarinic antagonist) (optionally atropine), an anticonvulsant (optionally benzodiazapene or diazepam), a pralidoxime (or 2-pyridine aldoxime methyl chloride, or 2-PAM) or a combination thereof.

In alternative embodiments, the invention provides products of manufacture or devices comprising a compound, composition or formulation of the invention, or a pharmaceutical composition or formulation of the invention, wherein optionally the product of manufacture or device is a medical device or an implant, wherein optionally the product of manufacture or device is designed to be capable of injecting, causing inhalation of, adsorption of, or otherwise administering for either enteral or parenteral administration a compound, composition or formulation of the invention, or a pharmaceutical composition or formulation of the invention.

In alternative embodiments, the invention provides a pump, a patch, a thin-film or dissolving film, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector, comprising a compound, composition or formulation of the invention, or a pharmaceutical composition or formulation of the invention.

In alternative embodiments, the invention provides methods for:

reactivating a butyrylcholinesterase (BChE) or an acetylcholinesterase (AChE or acetylhydrolase) inhibited by or conjugated to an ester of a phosphoric acid (EPA) or an organophosphate (OP), reactivating a BChE-OP or BChE-EPA conjugate or AchE-OP conjugate, protecting against irreversible inhibition of plasma or tissue BChE or AChE arising from an exposure to an organophosphate (OP), wherein optionally the exposure to is a bolus exposure to OP, ameliorating, diminishing, reversing, treating or preventing the toxic effects of an ester of a phosphoric acid (EPA) or an organophosphate (OP), wherein optionally the BChE comprises a human butyrylcholinesterase (hBChE) or the AChE comprises an acetylcholinesterase (h AChE), and optionally the reactivating is in vitro or in vivo, or the protecting is in vivo, comprising:

(a) providing a compound, composition or formulation of any of the invention, or a pharmaceutical composition or formulation of the invention, or a product of manufacture or device of the invention, or a pump, a patch, a thin-film or dissolving film, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector of claim 8; and (b) contacting a BChE-OP, AChE-OP or BChE-EPA conjugate (which optionally is an hBChE-OP, h AChE-OP or hBChE-EPA conjugate with the compound, composition or formulation of the invention, or administering or applying to an individual in need thereof a compound, composition or formulation of the invention, or a pharmaceutical composition or formulation of the invention, or a product of manufacture or device of the invention, or a pump, a patch, a thin-film or dissolving film, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector of the invention, wherein optionally the individual is a human, and optionally the contacting, administering or applying is as a single or as multiple bolus or dosage unit administrations, or as continuous contacting, administrations or applications, or any combination thereof, optionally including two or forms of contacting, administering or applying, optionally an IV, IM, oral and/or ophthalmic contacting, administering or applying in conjunction with, before and/or followed by a patch, a thin-film or dissolving film, a device controlled release or an IV infusion administration, thereby:

reactivating the butyrylcholinesterase (BChE) or an acetylcholinesterase (AChE or acetylhydrolase) inhibited by or conjugated to an ester of a phosphoric acid (EPA) or an organophosphate (OP), reactivating the BChE-OP or BChE-EPA conjugate or AChE-OP conjugate, protecting against irreversible inhibition of plasma or tissue BChE or AChE arising from an exposure to an organophosphate (OP), and/or ameliorating, diminishing, reversing, treating or preventing the toxic effects of an ester of a phosphoric acid (EPA) or an organophosphate (OP).

In alternative embodiments of methods of the invention, the contacting is in vitro or in vivo.

In alternative embodiments of methods of the invention, the organophosphate (OP) is a toxin, an herbicide, an insecticide, a pesticide, or a nerve gas or nerve agent, and optionally the organophosphate (OP) is a parathion, a malathion, a methyl parathion, a chlorpyrifos, a diazinon, a dichlorvos, a phosmet, a fenitrothion, a tetrachlorvinphos, an azamethiphos or an azinphos methyl, and optionally the OP or nerve agent comprises: a soman (O-Pinacolyl methylphosphonofluoridate); a tabun (also called GD) (ethyl N,N-Dimethylphosphoramidocyanidate); a sarin (or (RS)-propan-2-yl methyl phosphono fluoridate, also called "GB"); a cyclosarin (or (RS)-cyclohexyl methyl phosphono fluoridate, also calls "GF"); an O-ethyl S-[2-(diisopropylamino) ethyl]methyl phosphono thioate (also called VX); or, an N,N-diethyl-2-(methyl-(2-methyl propoxy) phosphoryl) sulfonyl ethanamine (also called VR, or Russian VX).

In alternative embodiments of methods of the invention, the compound, composition or formulation of the invention, or a pharmaceutical composition or formulation of the invention, or a product of manufacture or device of the invention, or a pump, a patch, a thin-film or dissolving film, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector of the invention, is co-administered with (optionally administered before, in conjunction with, and/or after administration of): (a) a butyrylcholinesterase (BChE), wherein optionally the BChE comprises a human butyrylcholinesterase (hBChE), or optionally the butyrylcholinesterase (BChE) comprise a recombinant BChE (rBChE) or a peptidomimetic BChE; or, (b) one or more additional drugs or formulations, wherein optionally the additional drug or formulation comprises a muscarinic acetylcholine receptor antagonist (a muscarinic antagonist) (optionally atropine), an anticonvulsant (optionally benzodiazapene or diazepam), a pralidoxime (or 2-pyridine aldoxime methyl chloride, or 2-PAM) or a combination thereof.

In alternative embodiments of methods of the invention, the compound, composition or formulation of the invention, or a pharmaceutical composition or formulation of the invention, or a product of manufacture or device of the invention, or a pump, a patch, a thin-film or dissolving film, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector of the invention, is administered or applied before OP exposure, optionally at least between about 1 to 60 minutes, or between about 15 to 30 min, before OP exposure, and then optionally is administered with more of the mixture immediately after the exposure, or optionally is administered with more of the mixture in intervals after the exposure.

In alternative embodiments, the invention provides kits comprising a compound, composition or formulation of the invention, or a pharmaceutical composition or formulation of the invention, or a product of manufacture or device of the invention, or a pump, a patch, a thin-film or dissolving film, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector of the invention, and/or optionally comprising ingredients and/or instructions for practicing a method of any of the invention.

In alternative embodiments, the invention provides uses of a compound, composition or formulation of any of the invention, in the preparation of medicament.

In alternative embodiments, the invention provides uses of a compound, composition or formulation of the invention, in the preparation of medicament for:

reactivating a butyrylcholinesterase (BChE) or an acetylcholinesterase (AChE or acetylhydrolase) inhibited by or conjugated to an ester of a phosphoric acid (EPA) or an organophosphate (OP), reactivating a BChE-OP or BChE-EPA conjugate or AchE-OP conjugate, protecting against irreversible inhibition of plasma or tissue BChE or AChE arising from an exposure to an organophosphate (OP), wherein optionally the exposure to is a bolus exposure to OP, and/or ameliorating, diminishing, reversing, treating or preventing the toxic effects of an ester of a phosphoric acid (EPA) or an organophosphate (OP), wherein optionally the BChE comprises a human butyrylcholinesterase (hBChE) or the AChE comprises an acetylcholinesterase (h AChE).

In alternative embodiments, the invention provides a combination, a drug combination, or a therapeutic combination, comprising: (a) a compound, composition or formulation of the invention, or a pharmaceutical composition or formulation of the invention; and (b) (i) a butyrylcholinesterase (BChE), wherein optionally the BChE comprises a human butyrylcholinesterase (hBChE), or optionally the butyrylcholinesterase (BChE) comprise a recombinant BChE (rBChE) or a peptidomimetic BChE; (ii) one or more additional drugs or formulations, wherein optionally the additional drug or formulation comprises a muscarinic acetylcholine receptor antagonist (a muscarinic antagonist) (optionally atropine), an anticonvulsant (optionally benzodiazapene or diazepam), a pralidoxime (or 2-pyridine aldoxime methyl chloride, or 2-PAM) or a combination thereof; or (iii) any combination thereof.

In alternative embodiments, compounds, compositions or formulations of the invention, or a pharmaceutical composition or formulation of the invention, are formulated to insure solubility and/or to avoid post-injection precipitation. Alternative embodiments comprise formulations and modes of administration for optimal deposition in the bronchioles, for example, including an aerosol spray or a powder or nanoparticle for inhalation. Alternative embodiments comprise formulations and modes of administration for controlled delivery, to prevent loss of accommodation reflex and blurred vision, and/or to insure prolonged scavenging or protection, for example, comprising an ophthalmic formulation or mode of administration, or a lotion or an ointment, or a patch, or a thin-film or dissolving film, comprising, e.g., nanoparticles, for epidermal or dermal administration or for controlled and/or sustained delivery.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of embodiments of the invention and are not meant to limit the scope of the invention as encompassed by the claims.

FIG. 2 illustrates Table 1, which includes schematics of structures of N-alkyl substituted imidazole oximes for OP-hBChE conjugates, and their reactivation rate constants at 0.67 mM formed by inhibition of hBChE by paraoxon and FluOP analogues of sarin, cyclosarin (CS) and VX; the data show dependence of reactivation on length of the oxime N-alkyl chain; normalized average (Norm. Avrg) $k_{obs}$ was calculated by averaging four $k_{obs}$ values for individual OPs, each expressed as percentage of the average $k_{obs}$ of six different oximes for that single OP; experiments were performed at 37° C. in 0.1 M phosphate buffer pH 7.4 in duplicates.

FIG. 3 illustrates Table 2, which includes schematics of structures of N-alkyl substituted imidazole oximes for OP-hBChE conjugates, and their reactivation rate constants at 0.67 mM formed by inhibition of hBChE by paraoxon and FluOP analogues of sarin, cyclosarin (CS) and VX; the data show dependence of reactivation substitution at the end of the oxime N-alkyl chain; oximes are ordered by the "Normalized Average" (Norm. Avrg) $k_{obs}$ calculated by averaging four $k_{obs}$ values for individual OPs, each expressed as percentage of the average $k_{obs}$ of thirteen different oximes for that single OP; values for 2PAM were not included in the averaging; experiments were performed at 37° C. in 0.1 M phosphate buffer pH 7.4 in duplicates.

FIG. 4 illustrates Table 3, which includes schematics of structures of N-alkyl substituted imidazole oximes for OP-hBChE conjugates, and their reactivation rate constants at 0.67 mM formed by inhibition of hBChE by paraoxon and FluOP analogues of sarin, cyclosarin (CS) and VX; the data show dependence of reactivation on substitution at the end of the oxime N-alkyl chain; the "Normalized Average" (Norm. Avrg) $k_{obs}$ was calculated by averaging four $k_{obs}$ values for individual OPs, each expressed as percentage of the average $k_{obs}$ of six different oximes for that single OP; values for 2PAM and Ta2OH were not included in the averaging; experiments were performed at 37° C. in 0.1 M phosphate buffer pH 7.4 in duplicates.

FIG. 5 illustrates Table 4, which includes schematics of structures of exemplary compounds of the invention, including N-alkyl substituted imidazole oximes, for OP-hBChE conjugates, and their reactivation rate constants at 0.67 mM formed by inhibition of hBChE by paraoxon and FluOP analogues of sarin, cyclosarin (CS) and VX; the data shows dependence of reactivation on substitution at the end of the oxime N-alkyl chain; the "Normalized Average" (Norm. Avrg) $k_{obs}$ was calculated by averaging four $k_{obs}$ values for individual OPs, each expressed as percentage of the average $k_{obs}$ of six different oximes for that single OP; values for 2PAM and Ta2OH were not included in the averaging; experiments were performed at 37° C. in 0.1 M phosphate buffer pH 7.4 in duplicates.

FIG. 6 illustrates a Table 5, which includes schematics of structures of exemplary compounds of the invention, including N-alkyl substituted imidazole oximes, for OP-hBChE conjugates, and their reactivation rate constants at 0.67 mM formed by inhibition of hBChE by paraoxon and FluOP analogues of sarin, cyclosarin (CS) and VX; the data also demonstrating in vivo efficacy of exemplary compounds of the invention, as discussed in detail in Example 2, below.

Like reference symbols in the various drawings indicate like elements.

Figure 1:
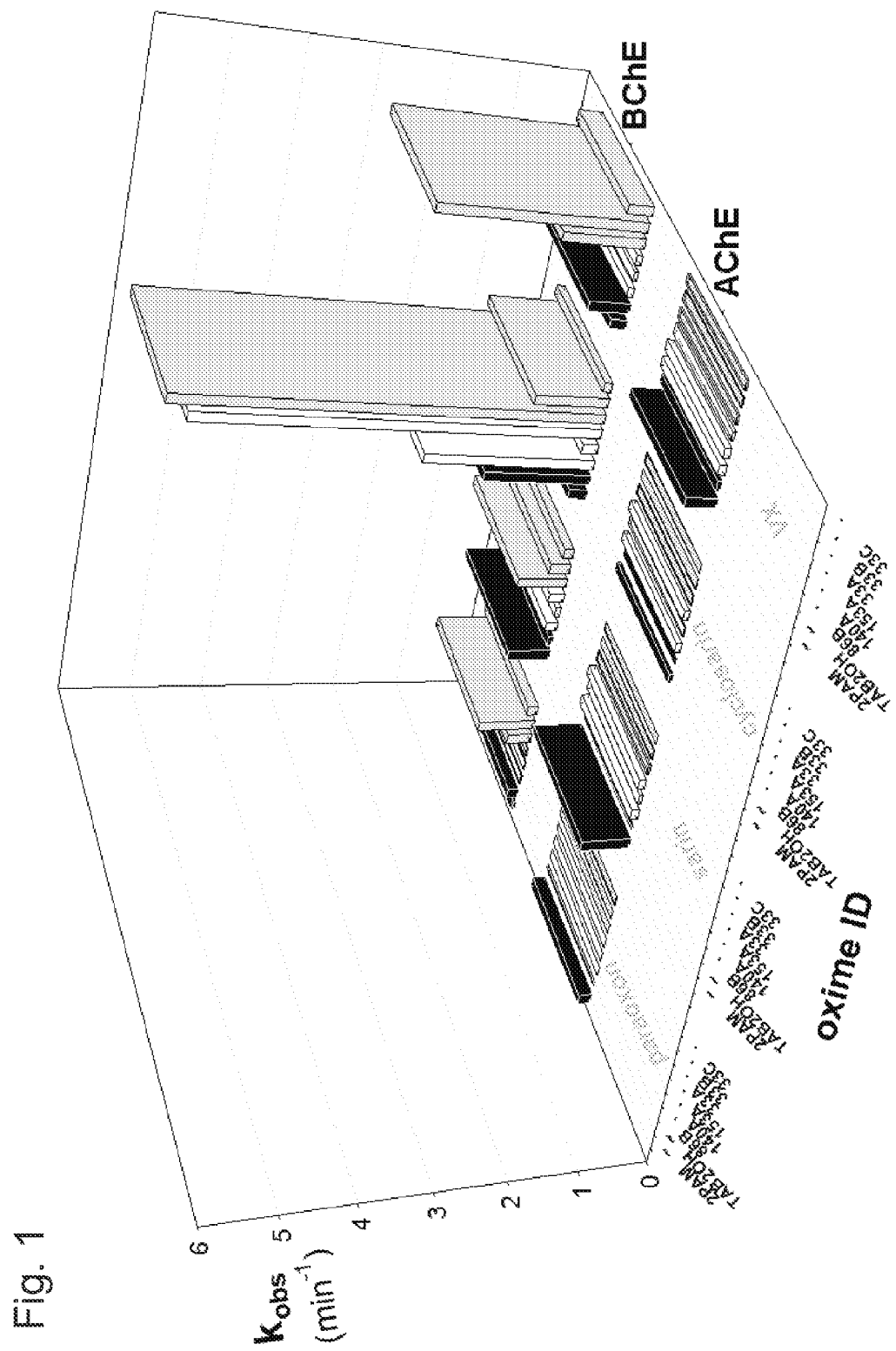
FIG. 1 graphically illustrates data from Tables 3 and 4, which summarize reactivation rate constants ($k_{obs}$) of six 0.67 mM N-alkyl substituted imidazole oximes for OP-hAChE and OP-hBChE conjugates formed by inhibition by paraoxon and FluOP analogues of sarin, cyclosarin and O-ethyl S-[2-(diisopropylamino) ethyl]methylphosphonothioate (also called VX); grey bars represent uncharged tertiary imidazole aldoximes, white bars cationic quaternary imidazolium aldoximes and black bars cationic references, pyridinium aldoxime 2PAM and nonpyridinium aldoxime TAB2OH.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides N-alkyl imidazole aldoximes, including cationic and uncharged tertiary imidazole aldoximes, and compositions and methods for making and using them, including methods for reactivating a human butyrylcholinesterase (hBChE) or an acetylcholinesterase (AChE or acetylhydrolase) inhibited by or conjugated to an ester of a phosphoric acid (EPA) or an organophosphate (OP), or reactivating a hBChE-OP or hBChE-EPA conjugate, or AChE-conjugate, by administration of a composition, formulation or device of the invention. In alternative embodiments, the invention provides methods comprising uses of compositions of the invention, which can comprise cationic and uncharged, imidazole-based nucleophilic antidote compounds, including N-alkyl imidazole aldoximes, including uncharged or zwitterionic tertiary imidazole aldoxime, reactivators of hAChE and hBChE, which are catalytic bioscavengers of organophosphates (OPs).

In alternative embodiments, while the invention is not limited by any particular mechanism of action, compounds of the invention can act as catalytic bioscavengers of organophosphates (OPs), and optionally are cationic and uncharged, imidazole based nucleophilic antidotes that reactivate human butyrylcholinesterase (hBChE) inhibited by OPs in, e.g., plasma, lungs and intestine of OP-exposed individuals, in order for a single hBChE molecule to repeatedly, covalently, bind and degrade multiple OP molecules. In alternative embodiments, compounds of the invention (including formulations, devices, etc. of the invention) are administered with endogenous or administered BChE (e.g., rBChE) to effective reduce toxic amounts of effectively toxic OP or to eliminate the OP from the circulation. The compounds of the invention are structurally novel scavengers that can serve as antidotes; they are structurally unrelated to currently used acetylcholinesterase (AChE) reactivators.

In alternative embodiments, compounds of the invention that as catalytic OP bioscavengers are administered with AChE mutants refractory to permanent catalytic incapacitation by dealkylation (aging) upon covalent OP inhibition. In combination with the effective cationic oxime reactivators of the invention, these AChE mutants will deplete fast aging OPs (e.g., such as soman and tabun) from the plasma of OP-exposed individuals, and can protect them from irreversible, permanent AChE inactivation. These reactivators will also reactivate native AChE inhibited by OP's, but at slower rates.

In alternative embodiments, the invention provides compounds, compositions, formulations, devices and methods for: treating, preventing or reversing the effects of OP-poisoning or OP exposure, e.g., resulting from accidental or intentional exposure to an OP or OP-comprising composition (e.g., a gas) such as an insecticide, an herbicide or a pesticide, or from a nerve agent exposure, e.g., accidental or as in warfare or a terrorist attack.

In alternative embodiments, compounds of the invention act as catalytic bioscavengers of organophosphates (OPs), and they can be used as cationic and/or uncharged, imidazole-based nucleophilic antidotes that can form zwitterions to reactivate human butyrylcholinesterase (hBChE) inhibited by OPs, e.g., in tissues, plasma, lungs and/or intestine of OP-exposed individuals. By administration of compounds of the invention, a single hBChE molecule can repeatedly and covalently bind and degrade multiple OP molecules, thereby effectively reducing or depleting OP from the circulation.

In alternative embodiments, catalytic OP bioscavengers of the invention are based on AChE mutants refractory to permanent catalytic incapacitation by dealkylation (aging) upon covalent OP inhibition. In alternative embodiments, the invention uses combinations of effective cationic oxime reactivators and AChE mutants to deplete fast aging OPs (soman, tabun) from the plasma of OP exposed individuals; e.g., protecting them from irreversible, permanent AChE inactivation. In alternative embodiments reactivators of the invention also reactivate native AChE inhibited by OP's, but at slower rates.

In alternative embodiments, compound of the invention can be formulated with or administered with a BChE, e.g., hBChE, which is currently used as stoichiometric OP bioscavenger. Due to the approximately 500-fold larger size of BChE molecules compared to nerve agent OP molecules, currently, very large amounts of highly purified BChE protein have to be used for effective protection resulting in prohibitively high costs of treatment and high risk of infection in field treatments, thus restricting its application to very small number of exposed individuals. In contrast, when administered with a catalytic bioscavengers compound of the invention, the expected (or effective) BChE dose can be reduced by an order of magnitude or more. In alternative embodiments, modified AChE and/or BChE are used, these have site-directed mutations to enable a faster catalytic turnover of OP and efficacy against wider spectrum of OP toxicants.

In alternative embodiments, compositions, compounds, formulations of the invention are formulated with, and methods of the invention comprise use of, a single site or double site human AChE mutant with reduced rates of aging. OP inhibition of the single site mutant is slower than a double mutant of this invention, and the oxime reactivation is slower. Hence, the double site mutant affords a higher turnover of enzyme.

While the invention is not limited by any particular mechanism of action, one alternative principle of the catalytic OP bioscavengers of this invention is to specifically and quickly capture offending OP molecules in circulation of exposed individuals and quickly convert them into nontoxic products. Human AChE and BChE are the best available macromolecular templates that can quickly and specifically react with OP toxicants and form stable, covalent, inactive conjugates, and use of exemplary compositions of this invention can restore the catalytic activity of AChE or BChE within short time frames (minutes). In alternative embodiments, compounds of the invention are designed as small, specific oxime nucleophiles to effectively interact with OP conjugates, thus reactivating the enzyme and releasing a non-toxic product from the conjugate.

In alternative embodiments, compounds of the invention, including the OP bioscavengers of the invention, are used as a preventative or prophylactic measure. In alternative embodiments, individuals expected to or highly likely to be exposed to OPs are treated, e.g., intravenously, topically or by inhalation, with a compound, formulation or device of the invention; which in alternative embodiments further comprise a BChE or an AChE enzyme, e.g., the combination comprising a bioscavenger mixture of the invention comprising an enzyme (e.g., a BChE or an AChE mutant) and a compound of the invention, e.g., a small molecule nucleophilic reactivator of the invention, e.g., about 15 to 30 min, but before OP exposure; and then in alternative embodiments are administered with more of the mixture immediately after and/or in continuing intervals after the exposure.

Because BChE is present in plasma at concentrations estimated to be 60 nM, administration of compounds of the invention can promote turnover the endogenous BChE-OP conjugates. Also, because some of the exemplary imidazole oximes of this invention have dissociation constant as low as 10 μM for the BChE enzyme, they also can serve to protect the unconjugated BChE from OP inactivation.

In alternative embodiments the invention provides oral administration of exemplary compositions of this invention, e.g., small molecule uncharged reactivators, highly efficient for reactivation of OP-inhibited native tissue hBChE. In alternative embodiments, this treatment provides protection from intoxication by effectively degrading offending OP molecules. In alternative embodiments, compounds of the invention, including the bioscavenger mixture(s) of the invention, are effective when administered after OP exposure, as well as in situations when OP concentrations in the circulation of exposed individuals reach high levels due to a massive OP exposure. Clearing excess offending OP can be a critical prerequisite to effective treatment of OP exposed patients. In alternative embodiments, since the OP's can partition into lipids and leach from those sites, scavenging should continue with administration of more compounds of the invention after the initial exposure period of high toxicity.

In alternative embodiments, compositions of the invention further comprise, and/or methods of the invention further comprise use of (e.g., are formulated with or administered with), compounds as set forth in Table 1, Table 2 and/or Table 3, including 2-hydroxyiminomethyl imidazole analogs and bioisosteres thereof. These exemplary 2-hydroxyiminomethyl imidazoles and imidazoliums are close congeners in which various substituted alkyl groups are found at the 1-nitrogen position of the respective imidazole 2-aldoximes or 3-methyl imidazolium 2-aldoximes.

In alternative embodiments, the invention provides compounds, compositions and formulations that act as antidotes to organophosphate insecticide exposure, e.g., as the organophosphates widely used in agriculture.

In alternative embodiments, the invention provides compounds, compositions and formulations that act as a universal antidote to non-aging nerve agents, e.g., that would be used as countermeasures to chemical terrorism, e.g., as has occurred in the Japanese subway system and in communities in Syria. The invention provides a superior agent that refines structure-activity considerations further and moves BChE to becoming a catalytic rather than a stoichiometric scavenger. In alternative embodiments the value of the compounds, compositions and formulations of the invention is to dissuade terrorists from synthesizing organophosphates by limiting their toxicity and threat potential and minimizing the amount of BChE necessary for antidotal scavenging.

In alternative embodiments, compounds, compositions and formulations of the invention are administered to individuals exposed to a high concentration of organophosphate, e.g., through inhalation; without such administration, a high bolus OP exposure dose would irreversibly inhibit all the cholinesterases in plasma and tissue. However, in this alternative embodiment, the compound of the invention is acting as a reversible inhibitor (e.g., in the animal or subject); thus, the irreversible inhibition of enzyme by the OP toxin will not be complete because of the competition with "reversible inhibitor" compounds of the invention. Thus, as the excess organophosphate disappears from the animal (e.g., human) either through the respiratory system or by catalytic hydrolysis, the residual cholinesterase that was only reversibly inhibited will again become active. Moreover, to keep the subject functional after exposure requires only a small fraction of the cholinesterase to be active, and administration of a compound of the invention results in maintaining that vital, functional fraction. In other words, by administration of a compound of the invention, the animal or subject now can have an "enzyme reserve" that allows cholinergic neurotransmission central and peripheral nervous systems to remain functional. In this alternative embodiment, in this way, the compound of the invention is acting as a reversible inhibitor and acts as a protectant.

In alternative embodiments, some exemplary compounds of the invention have a sufficiently low $K_{ox}$ so as to consider them as working in this mechanism, i.e., maintaining an "enzyme reserve". In alternative embodiments, some exemplary compounds of the invention have an enhancing antidotal or scavenging activity; this has been called the "pyridostigmine effect" (where pyridostigmine is a semi-reversible inhibitor and does protect against organophosphate exposure). Thus, in alternative embodiments, compounds of the invention are used in mixtures, or "antidote cocktails", thereby contributing to cumulative inhibition.

Bioisosteres of Compounds of the Invention

In alternative embodiments, the invention also provides bioisosteres of compounds of the invention. In alternative embodiments, bioisosteres of the invention are compounds of the invention comprising one or more substituent and/or group replacements with a substituent and/or group having substantially similar physical or chemical properties which produce substantially similar biological properties to a compound of the invention, or stereoisomer, racemer or isomer thereof. In one embodiment, the purpose of exchanging one bioisostere for another is to enhance the desired biological or physical properties of a compound without making significant changes in chemical structures.

For example, in one embodiment, bioisosteres of compounds of the invention are made by replacing one or more hydrogen atom(s) with one or more fluorine atom(s), e.g., at a site of metabolic oxidation; this may prevent metabolism (catabolism) from taking place. Because the fluorine atom is similar in size to the hydrogen atom the overall topology of the molecule is not significantly affected, leaving the desired biological activity unaffected. However, with a blocked pathway for metabolism, the molecule may have a longer half-life or be less toxic, and the like.

Formulations and Pharmaceutical Compositions

In alternative embodiments, the invention provides compounds and compositions, including formulations and pharmaceutical compositions, for use in in vivo, in vitro or ex vivo methods, e.g., for reactivating a butyrylcholinesterase (BChE) or an acetylcholinesterase (AChE or acetylhydrolase) inhibited by or conjugated to an ester of a phosphoric acid (EPA) or an organophosphate (OP); or, reactivating a BChE-OP or BChE-EPA conjugate or AChE-OP conjugate; or, protecting against irreversible inhibition of plasma or tissue BChE or AChE arising from an exposure to an organophosphate (OP), wherein optionally the exposure to is a bolus exposure to OP; or, ameliorating, diminishing, reversing, treating or preventing the toxic effects of an ester of a phosphoric acid (EPA) or an organophosphate (OP).

In alternative embodiments, the pharmaceutical compositions of the invention can be administered parenterally, topically, orally or by local administration, such as by aerosol or transdermally. In alternative embodiments, pharmaceutical compositions can be prepared in various forms, such as granules, tablets, pills, capsules, suspensions, taken orally, suppositories and salves, lotions and the like. Pharmaceutical formulations of this invention may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, geltabs, on patches, in a thin-film or dissolving film, in implants, etc. In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In alternative embodiment, compositions of the invention are delivered orally, e.g., as pharmaceutical formulations for oral administration, and can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Oral carriers can be elixirs, syrups, capsules, tablets, pills, geltabs and the like. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, dextrins, or a salt thereof, such as sodium alginate.

In alternative embodiments, liquid carriers are used to manufacture or formulate compounds of this invention, or a composition used to practice the methods of this invention, including carriers for preparing solutions, suspensions, emulsions, syrups, elixirs and pressurized compounds. The active ingredient (e.g., a composition of this invention) can be dissolved or suspended in a pharmaceutically acceptable liquid carrier such as water, an organic solvent, a mixture of both or pharmaceutically acceptable oils or fats. The liquid carrier can comprise other suitable pharmaceutical additives such as solubilizers, emulsifiers, buffers, preservatives, sweeteners, flavoring agents, suspending agents, thickening agents, colors, viscosity regulators, stabilizers or osmo-regulators.

In alternative embodiments, solid carriers are used to manufacture or formulate compounds of this invention, or a composition used to practice the methods of this invention, including solid carriers comprising substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

In alternative embodiments, compounds and pharmaceutical compositions of the invention are formulated as and/or delivered as patches, e.g., a transdermal patch or a medicated adhesive patch that is placed on the skin or mucous membrane to deliver a specific dose of drug or medication (e.g., compounds and pharmaceutical compositions of the invention) through the skin and into the bloodstream. An advantage of a transdermal drug delivery route over other types of medication delivery such as oral, topical, intravenous, intramuscular, etc. can be that the patch provides a controlled release of the drug or medication into the patient, optionally through either a porous membrane covering a reservoir of medication or through body heat melting thin layers of medication embedded in the adhesive.

In alternative embodiments, a patch is a single-layer drug-in-adhesive patch; in this exemplary embodiment, the adhesive layer also contains the drug or medication (e.g., compounds and pharmaceutical compositions of the invention). In this type of patch the adhesive layer can not only serves to adhere the various layers together, along with the entire system to the skin, but also can be responsible for the releasing of the drug or medication. The adhesive layer can be surrounded by a temporary liner and a backing.

In alternative embodiments, a patch is a multi-layer drug-in-adhesive patch, which is similar to the single-layer system, but it adds another layer of drug-in-adhesive, optionally separated by a membrane. One of the layers can be for immediate release of a drug or medication (e.g., compounds and pharmaceutical compositions of the invention) and other layer is for control release of the same and/or different drug or medication from the reservoir. This patch also can have a temporary liner-layer and a permanent backing. In alternative embodiments, drug release depends on membrane permeability and diffusion of drug molecules.

In alternative embodiments, a patch is a reservoir transdermal system, which has a separate drug layer; the drug layer can be a liquid or gel compartment comprising a drug solution or a suspension separated by the adhesive layer. The drug reservoir can be totally encapsulated in a shallow compartment molded from a drug-impermeable metallic plastic laminate, optionally with a rate-controlling membrane made of a polymer (e.g., a vinyl acetate) on one surface. This patch also can be backed by a backing layer. In a reservoir transdermal system the rate of release can be designed to be zero order.

In alternative embodiments, a patch is a matrix system, or so-called "monolithic device", which comprises a drug layer of a solid or a semisolid matrix comprising a drug solution or a suspension (e.g., comprising compounds and pharmaceutical compositions of the invention). The adhesive layer in this patch can surround the drug layer, optionally partially overlaying it.

In alternative embodiments, compounds and pharmaceutical compositions of the invention are formulated as and/or delivered as or in so-called "thin-film" or dissolving film delivery systems. These can be used to administer a drug solution or a suspension (e.g., comprising compounds and pharmaceutical compositions of the invention) via absorption in the mouth (e.g., buccally or sublingually) and/or via the small intestines or otherwise enterically. A film can be prepared using a hydrophilic polymer that rapidly dissolves on a mucous membrane, e.g., in the tongue or buccal cavity or esophagus or intestine, thus delivering the drug to the systemic circulation via dissolution when contact with liquid (e.g., a bodily fluid) is made.

In alternative embodiments, thin-film drug delivery is used as an alternative to or with another delivery modality, e.g., tablets, capsules, liquids and the like. They can be similar in size, shape and thickness to a postage stamp, and can be designed for oral administration, with the user placing the strip on or under the tongue (sublingual) or along the inside of the cheek (buccal). As the strip dissolves, the drug can enter the blood stream enterically, buccally or sublingually. In alternative embodiments, thin-films are made of combination of microcrystalline cellulose and maltodextrin, and can also include plasticizers, phthalate, glycols.

In alternative embodiments, concentrations of therapeutically active compound in a formulation can be from between about 0.1% to about 100%, e.g., having at least about 0.5%, 1%, 5%, 10%, 20%, 30%, 40%, 50%, 55%, 60%, 65%, 70%, 75%, 80%, 85%, 90%, 95%, or 99%, or more, by weight.

In alternative embodiments, therapeutic formulations are prepared by any method well known in the art, e.g., as described by Brunton et al., eds., Goodman and Gilman's: The Pharmacological Bases of Therapeutics, 12th ed., McGraw-Hill, 2011; Remington: The Science and Practice of Pharmacy, Mack Publishing Co., 20th ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

In alternative embodiments, therapeutic formulations are delivered by any effective means appropriated for a particular treatment. For example, depending on the specific antitumor agent to be administered, the suitable means include oral, rectal, vaginal, nasal, pulmonary administration, or parenteral (including subcutaneous, intramuscular, intravenous and intradermal) infusion into the bloodstream. For parenteral administration, antitumor agents of the present invention may be formulated in a variety of ways. Aqueous solutions of the modulators can be encapsulated in polymeric beads, liposomes, nanoparticles or other injectable depot formulations known to those of skill in the art. In alternative embodiments, compounds of the invention are administered encapsulated in liposomes. In alternative embodiments, depending upon solubility, compositions are present both in an aqueous layer and in a lipidic layer, e.g., a liposomic suspension. In alternative embodiments, a hydrophobic layer comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The pharmaceutical compositions can be formulated in any way and can be administered in a variety of unit dosage forms depending upon the condition or disease and the degree of illness, the general medical condition of each patient, the resulting preferred method of administration and the like. For example, in adults, an exemplary dosage may be about 30 mg/kg administered e.g., by intravenous therapy, e.g., over between about 15 to 30 minutes, or by intramuscular injection or subcutaneous injection, e.g., repeated later in intervals, e.g., at about 60 minutes later. In alternative embodiments, an exemplary dosage and administration is as a 500 mg/h continuous IV infusion. In alternative embodiments, for children, an exemplary dosage and administration is at between about 20 to 50 mg/kg, optionally followed by a maintenance infusion at between about 5 to 10 mg/kg/h.

Details on techniques for formulation and administration are well described in the scientific and patent literature, see, e.g., the latest edition of *Remington's Pharmaceutical Sciences*, Maack Publishing Co., Easton Pa. ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice this invention can be in forms such as tablets, pills, powders, capsules, liquids, gels, syrups, slurries, suspensions, etc., suitable for in vivo, in vitro or ex vivo applications.

In practicing this invention, the compounds (e.g., formulations) of the invention can comprise a solution of compounds of the invention, including stereoisomers, derivatives and analogs thereof, disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations of the invention can be delivered by the use of liposomes. In alternative embodiments, by using liposomes, particularly where the liposome surface carries ligands specific for target cells or organs, or are otherwise preferentially directed to a specific tissue or organ type, one can focus the delivery of the active agent into a target cells in an in vivo, in vitro or ex vivo application.

The compositions and formulations of the invention can be directly administered, e.g., under sterile conditions, to an individual (e.g., a patient) to be treated. The modulators can be administered alone or as the active ingredient of a pharmaceutical composition. Compositions and formulations of this invention can be combined with or used in association with other therapeutic agents. For example, an individual may be treated concurrently with conventional therapeutic agents.

In alternative embodiments, a compound, a formulation or mixture of compounds of the invention is/are administered parenterally in an appropriate co-solvent to enable distribution from the site of IM, SC or IV injection, to prevent post-injection precipitation by virtue of a change in pH, for example, as described in J. Pharm. Pharmacol: 62:873-82 (2010); Adv. Drug Delivery Rev. 59:603-07 (2007), and to ensure "solubilization" conditions at the injection site, e.g., as described in J. Pharm. Pharmacol 62: 1607-21; Anesth Analg 79: 933-39 (1994); J. Pharm. Pharmacol 65 1429-39 (2013). Although these compounds with two ionization equilibria can form zwitterions, the predominant species is uncharged at physiologic pH. Similar to certain parenteral anesthetics, the compounds of the invention can be administered at low pH (e.g., between about pH 4 to 6) or high pH (e.g., between about pH 8 to 11). Hence these alternative embodiments involve: Low pH solutions adjusted with acetic acid; High pH solutions adjusted with $Na_2CO_3$ (pH 10-11); Co-solvent formulation at neutral pH to include propylene glycol (up to 50%), polyethylene glycol, 2-hydroxypropyl β-cyclodextrin and combinations and congeners thereof; and/or, micellular dispersions with surface active agents.

These approaches can insure more rapid systemic absorption from the sites of administration. The above references document enhanced rates of absorption using these procedures for drugs of similar solubility: ketamine, etomidate, thiopental, diclofenac, aripiprazole, carbamazepine.

In alternative embodiments, oral (p.o.) preparations encompass tablets and capsules, including syrups emulsions and suspensions to insure distribution throughout the gastrointestinal (GI) tract. In alternative embodiment, oral preparations are employed for:
  a) protection when exposure is likely based on release and wind currents or distribution through a built ventilation system, such as a subway;
  b) as an adjunct to antidotal agents to protect plasma BChE and tissue AChE from being irreversibly inhibited by transient occupation of the binding site.
c) initial loading doses in subjects that are conscious and not experiencing nausea and vomiting,
d) subsequent maintenance dosing after an initial parenteral loading dose. Oral administration over periods of days may also facilitate clearance of the lipophilic organophosphate from the body. Some of the OP may be stored in lipid reservoirs (adipose tissue, myelin) and be scavenged as it dissociates from these sites.

In alternative embodiments, the exemplary imidazole and -methyl imidazolium 2-aldoximes of the invention are designed to reactivate endogenous plasma BChE or assist the catalysis of the organophosphate by administered BChE.

Compounds and formulations of the invention can be administered by parental or pulmonary routes, mixtures of these compounds with tissue tertiary amine antidotes, such as the so-called exemplary RS194B, RS138B, and quaternary pyridinium aldoximes, such as HI6 and MMB4, may also be also indicated. Hence, combinations of antidotal and scavenging agents may be an advantageous combination therapy, depending on the organophosphate and the route of exposure (dermal, pulmonary and GI, e.g., the latter can arise from attempted suicide or homicide).

Nanoparticles, Nanolipoparticles and Liposomes

The invention also provides nanoparticles, nanolipoparticles, vesicles and liposomal membranes comprising compounds and compositions used to practice the methods of this invention.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice this invention.

Liposomes can be made using any method, e.g., as described in Park, et al., U.S. Pat. Pub. No. 20070042031, including method of producing a liposome by encapsulating an active agent (e.g., a compound of the invention), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound (e.g., e.g., a compound of the invention) used to practice this invention to a desired cell type or organ, e.g., brain, as described e.g., in U.S. Pat. Pub. No. 20070110798.

The invention also provides nanoparticles comprising compounds (e.g., a compound of the invention) used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice this invention to mammalian cells in vivo, in vitro or ex vivo, as described, e.g., in U.S. Pat. Pub. No. 20050136121.

Dosaging

The pharmaceutical compositions and formulations of the invention can be administered for prophylactic and/or therapeutic treatments. In therapeutic applications, compositions are administered to a subject already exposed to an OP or an OP-comprising toxin in an amount sufficient to cure, alleviate or partially arrest the clinical manifestations of the agent and/or its complications (a "therapeutically effective amount"). The pharmaceutical compositions and formulations of the invention also can be administered as a preventative agent, e.g., prophylactically.

The amount of pharmaceutical composition adequate to accomplish this is defined as a "therapeutically effective dose." The dosage schedule and amounts effective for this use, i.e., the "dosing regimen," will depend upon a variety of factors, including the stage of the exposure, the severity of the exposure, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient and particular active agent. Guidelines provided for similar compositions used as pharmaceuticals can be used as guidance to determine the dosage regiment, i.e., dose schedule and dosage levels, administered practicing the methods of the invention are correct and appropriate.

Products of Manufacture, Kits

The invention also provides products of manufacture and kits for practicing the methods of this invention, and comprising compounds, compositions and formulations of this invention, including bioisostere compounds of the invention. In alternative embodiments, the invention provides products of manufacture and kits comprising compounds, compositions and formulations of this invention, and comprising all the components needed to practice a method of the invention.

The invention provides kits comprising compounds, compositions and formulations of this invention, and comprising compositions and/or instructions for practicing methods of the invention. In alternative embodiments, the invention provides kits comprising: a composition used to practice a method of any of the invention, optionally comprising instructions for use thereof.

In alternative embodiments, the invention provides pumps, devices, subcutaneous infusion devices, continuous subcutaneous infusion device, infusion pens, needles, reservoirs, ampoules, vials, syringes, cartridges, disposable pen or jet injectors, prefilled pens or syringes or cartridges, cartridge or disposable pen or jet injectors, two chambered or multi-chambered pumps, syringes, cartridges or pens or jet injectors comprising a composition, composition or a formulation of the invention. In alternative embodiments, the injector is an autoinjector, e.g., a SMARTJECT® autoinjector (Janssen Research and Development LLC); or a MOLLY®, or DAI®, or DAI-RNS® autoinjector (SHL Group, Deerfield Beach, Fla.). In alternative embodiments, the injector is a hypodermic or a piston syringe.

The invention will be further described with reference to the examples described herein; however, it is to be understood that the invention is not limited to such examples.

EXAMPLES

Example 1: Exemplary Combinations of the Invention

This example describes exemplary combinations of the invention, and methods for making and using (administering) them.

While the invention is not limited by any particular mechanism of action, catalytic bioscavengers of organophosphates (OPs) of the invention are based on action of uncharged tertiary imidazole aldoximes, or cationic nucleophilic, antidotes that reactivate human butyrylcholinesterase (hBChE) or human AChE mutant activities inhibited by OPs in plasma of OP-exposed individuals. Use of compounds of the invention allow a single hBChE or hAChE molecule to repeatedly, covalently bind and degrade multiple OP molecules, effectively depleting the OP from the circulation of an individual.

Joint administration of hBChE and an efficient oxime reactivator of the invention (e.g., an uncharged tertiary imidazole aldoxime) of OP-hBChE can reduce mass of hBChE protein needed for efficient protection by orders of magnitude by establishing a "catalytic bioscavenger" system.

We demonstrated both in vitro and in vivo feasibility of a catalytic bioscavenger composed of purified hBChE and a cationic nonpyridinium aldoxime TAB2OH. While allowing for reduction of administered effective hBChE doses, the protective effects of the cationic nonpyridinium aldoxime TAB2OH catalytic bioscavenger were relatively small due to relatively low reactivation potency of TAB2OH.

In alternative embodiments, the invention provides N-alkyl imidazole aldoximes, including uncharged tertiary imidazole aldoximes, as reactivators of hBChE. We here first characterize in vitro reactivation properties of a family of uncharged tertiary imidazole aldoximes against four different OP-hBChE conjugates resulting from sarin, cyclosarin, O-ethyl S-[2-(diisopropylamino) ethyl]methylphosphonothioate (also called VX), and paraoxon covalent inhibition, and proceed with optimization of their structure to yield highly efficient OP-hBChE reactivators, orders of magnitude faster than any of those previously described, see FIG. 6. In alternative embodiments, the presence of a neutral species at physiological pH values between about 4 and 9 assures that these tertiary imidazole aldoximes provide for a reasonable level of oral bioavailability. Similarly, this should allow for passage of the compounds across the blood-brain barrier, so that reactivation of OP conjugates of AChE is limited only by the kinetic parameters of reactivation and not passing the blood-brain barrier. Coupling the high reactivation rates with the good bioavailability of the uncharged tertiary imidazole aldoximes of the invention allows for simple and inexpensive production, storage, distribution, chemical stability, and fast and easy administration of corresponding anti-nerve agent countermeasure.

Preparation of Novel Oximes

All reactions were performed with commercially available ACS grade reagents and solvents. Anhydrous N,N-dimethylfomamide (DMF), acetonitrile and nitromethane were used as received without further purification. 1H NMR and 13C NMR spectra were recorded on a Varian 400 MHz spectrometer. All chemical shifts were reported in ppm relative to solvent resonances, as indicated (DMSO-d6 d 2.49, 1H; d 39.49, 13C), (CDCl3 d 7.26, 1H; d 77.0, 13C). 1H NMR coupling constants (J) are given in Hz. The following compounds were synthesized by known literature methods; 5-bromopenta-1,3-diene1 and 1-bromohexa-2,4-diene2.

A. General method for preparation of imidazole oximes RS2-33A, RS2-33C, RS2-33B, RS2-37B, RS138B, RS136A, RS92B, RS3-25C and RS3-20C. To a mixture of formylimidazole 1 and $K_2CO_3$ in DMF, the required bromide or mesylate was added and the reaction mixture was stirred overnight under atmosphere of nitrogen at rt. The resulting suspension was cooled to room temperature (rt) and filtered. Water was added to the filtrate and the resulting solution was extracted with Et2O (3×25 mL). The organic layer was dried over MgSO4 and evaporated to give the corresponding alkylimidazole-2-carbaldehyde.

Hydroxylamine hydrochloride (1.5 equiv) was dissolved in water and neutralized with Na2CO3 (1.5 equiv). Alkylimidazole-2-carbaldehyde was added to the solution of hydroxylamine, and the reaction mixture was stirred at rt for 1 h. The resulting precipitate of the corresponding oxime was filtered out, rinsed with water and dried over $P_2O_5$ under vacuum.

1-(Pent-4-en-1-yl)imidazole-2-carbaldehyde oxime (RS2-33A). Prepared according to the general method A using formylimidazole 1 (0.50 g, 5.2 mmol), $K_2CO_3$ (0.72 g, 5.2 mmol), and 5-bromopent-1-ene (0.93 g, 6.2 mmol) in DMF (20 mL). Yellow oil 2a (0.55 g, 64%).

1-(Pent-4-en-1-yl)imidazole-2-carbaldehyde (2a) 0.50 g (3 mmol), NH2OH.HCl 0.31 g (4.5 mmol), water (5 mL), Na2CO3 0.48 g (4.5 mmol). White solid, yield (0.47 g, 87%).

1H NMR (400 MHz, DMSO-d6) δ 11.46 (s, 1H), 8.04 (s, 1H), 7.31 (s, 1H), 7.00 (s, 1H), 5.85-5.75 (m, 1H), 5.07-4.94 (m, 2H), 4.23 (t, J=8 Hz, 2H), 2.00 (q, J=8 Hz, 2H), 1.77 (pent, J=8 Hz, 2H); 13C NMR (400 MHz, DMSO-d6) δ 141.3, 139.6, 137.6, 128.8, 123.7, 115.4, 46.2, 30.0, 29.4; LCMS (ESI) (m/z): [M+H]+ calculated for C10H17N3O, 196.3. found, 196.4.

1-(3-Phenylpropyl)imidazole-2-carbaldehyde oxime (RS2-33C). Prepared according to the general method A using formylimidazole 1 (0.50 g, 5.2 mmol), $K_2CO_3$ (0.72 g, 5.2 mmol), and (3-bromopropyl)benzene (1.2 g, 6.2 mmol) in DMF (20 mL). Yellow oil 2b (0.77 g, 69%).

1-(3-Phenylpropyl)imidazole-2-carbaldehyde (2b) 0.64 g (3 mmol), NH2OH.HCl 0.31 g (4.5 mmol), water (5 mL), Na2CO3 0.48 g (4.5 mmol). White solid, yield (0.58 g, 84%).

1H NMR (400 MHz, DMSO-d6) δ 11.47 (s, 1H), 8.05 (s, 1H), 7.34 (s, 1H), 7.28 (t, J=8 Hz, 2H), 7.18 (app d, J=8 Hz, 3H), 7.01 (s, 1H), 4.27 (t, J=8 Hz, 2H), 2.55 (t, J=8 Hz, 2H), 1.99 (pent, J=8 Hz, 2H); 13C NMR (400 MHz, DMSO-d6) δ 141.3, 141.0, 139.6, 128.8, 128.4, 128.1, 125.9, 123.6, 46.5, 32.0, 31.9; LCMS (ESI) (m/z): [M+H]+ calculated for C10H17N3O, 196.3. found, 196.4.

1-(3,3-dimethylbutyl)imidazole-2-carbaldehyde oxime (RS2-33B). Prepared according to the general method A using formylimidazole 1 (0.50 g, 5.2 mmol), $K_2CO_3$ (0.72 g, 5.2 mmol), and 1-bromo-3,3-dimethylbutane (1 g, 6.2 mmol) in DMF (20 mL). Yellow oil 2c (0.57 g, 61%).

1-(3,3-dimethylbutyl)imidazole-2-carbaldehyde (2c) 0.54 g (3 mmol), NH2OH.HCl 0.31 g (4.5 mmol), water (5 mL), Na2CO3 0.48 g (4.5 mmol). White solid, yield (0.52 g, 89%). 1H NMR (400 MHz, DMSO-d6) δ 11.42 (s, 1H), 8.02 (s, 1H), 7.33 (s, 1H), 6.98 (s, 1H), 4.25 (pent, J=4 Hz, 2H), 1.56 (pent, J=4 Hz, 2H), 0.93 (s, 9H); 13C NMR (400 MHz, DMSO-d6) δ 141.3, 139.4, 128.8, 123.4, 44.3, 43.6, 29.7, 29.2;

1-Isopentyl imidazole-2-carbaldehyde oxime (RS2-37B). Prepared according to the general method A using formylimidazole 1 (0.50 g, 5.2 mmol), $K_2CO_3$ (0.72 g, 5.2 mmol), and 1-bromo-3-methylbutane (0.94 g, 6.2 mmol) in DMF (20 mL). Yellow oil 2d (0.61 g, 71%).

1-isopentyl imidazole-2-carbaldehyde (2d) 0.50 g (3 mmol), NH2OH.HCl 0.31 g (4.5 mmol), water (5 mL), Na2CO3 0.48 g (4.5 mmol). White solid, yield (0.44 g, 81%).

1H NMR (400 MHz, DMSO-d6) δ 11.42 (s, 1H), 8.03 (s, 1H), 7.32 (s, 1H), 6.99 (s, 1H), 4.25 (t, J=8 Hz, 2H), 1.59-1.46 (m, 3H), 0.9 (d, J=4 Hz, 6H); 13C NMR (400 MHz, DMSO-d6) δ 141.4, 139.5, 128.8, 123.5, 45.1, 25.1, 22.3;

1-(2-Morpholinoethyl) imidazole-2-carbaldehyde oxime (RS204B). Prepared according to the general method A using formylimidazole 1 (0.50 g, 5.2 mmol), $K_2CO_3$ (0.72 g, 5.2 mmol), and 2-morpholinoethyl methanesulfonate (1.30 g, 6.2 mmol) in DMF (20 mL). Yellow oil 2e (0.75 g, 69%).

1-(2-Morpholinoethyl) imidazole-2-carbaldehyde (2e) 0.63 g (3 mmol), NH2OH.HCl 0.31 g (4.5 mmol), water (5 mL), Na2CO3 0.48 g (4.5 mmol). White solid, yield (0.52 g, 77%). 1H NMR (400 MHz, DMSO-d6) δ 11.46 (s, 1H), 8.03 (s, 1H), 7.32 (s, 1H), 6.98 (s, 1H), 4.34 (t, J=8 Hz, 2H), 2.69 (t, J=8 Hz, 2H), 2.45 (app s, 4H), 1.65 (app s, 4H); 13C NMR (400 MHz, DMSO-d6) δ 141.4, 139.5, 128.6, 124.0, 55.8, 53.6, 45.7, 23.1;

1-(3-Azidopropyl) imidazole-2-carbaldehyde oxime (RS138B). Prepared according to the general method A using formylimidazole 1 (0.50 g, 5.2 mmol), $K_2CO_3$ (0.72 g, 5.2 mmol), and 3-azidopropyl methanesulfonate (1.1 g, 6.2 mmol) in DMF (20 mL). Yellow oil 2f (0.62 g, 67%).

1-(3-Azidopropyl) imidazole-2-carbaldehyde (2f) 0.54 g (3 mmol), NH2OH.HCl 0.31 g (4.5 mmol), water (5 mL), Na2CO3 0.48 g (4.5 mmol). White solid, yield (0.46 g, 79%). 1H NMR (400 MHz, DMSO-d6) δ 11.48 (s, 1H), 8.05 (s, 1H), 7.32 (s, 1H), 7.01 (s, 1H), 4.29 (t, J=8 Hz, 2H), 3.33 (t, J=8 Hz, 2H), 1.94 (pent, J=8 Hz, 2H); 13C NMR (400 MHz, DMSO-d6) δ 141.3, 139.6, 128.9, 123.7, 47.9, 44.2, 29.4;

1-(3-Azidobutyl) imidazole-2-carbaldehyde oxime (RS136A). Prepared according to the general method A using formylimidazole 1 (0.50 g, 5.2 mmol), $K_2CO_3$ (0.72 g, 5.2 mmol), and 3-azidobutyl methanesulfonate (1.2 g, 6.2 mmol) in DMF (20 mL). Yellow oil 2g (0.68 g, 68%).

1-(3-Azidobutyl) imidazole-2-carbaldehyde (2g) 0.58 g (3 mmol), NH2OH.HCl 0.31 g (4.5 mmol), water (5 mL), Na2CO3 0.48 g (4.5 mmol). White solid, yield (0.55 g, 88%). 1H NMR (400 MHz, DMSO-d6) δ 11.54 (s, 1H), 8.06 (s, 1H), 7.33 (s, 1H), 7.02 (s, 1H), 4.26 (t, J=8 Hz, 2H), 3.34 (t, J=8 Hz, 2H), 1.73 (pent, J=8 Hz, 2H), 1.47 (pent, J=8 Hz, 2H); 13C NMR (400 MHz, DMSO-d6) δ 141.2, 139.5, 128.6, 123.7, 50.2, 46.1, 27.5, 25.3;

1-(3-Prop-2-yn-1-yl) imidazole-2-carbaldehyde oxime (RS92B). Prepared according to the general method A using formylimidazole 1 (0.50 g, 5.2 mmol), $K_2CO_3$ (0.72 g, 5.2 mmol), and propargyl bromide 80 wt % solution in toluene (0.67 mL, 6.2 mmol) in DMF (20 mL). Yellow oil 2h (0.49 g, 70%).

1-(3-Prop-2-yn-1-yl) imidazole-2-carbaldehyde (2h) 0.40 g (3 mmol), NH2OH.HCl 0.31 g (4.5 mmol), water (5 mL), Na2CO3 0.48 g (4.5 mmol). White solid, yield (0.35 g, 78%). 1H NMR (400 MHz, DMSO-d6) δ 11.61 (s, 1H), 8.06 (s, 1H), 7.39 (s, 1H), 7.03 (s, 1H), 5.14 (d, J=4 Hz, 2H), 3.46 (d, J=4 Hz, 2H); 13C NMR (400 MHz, DMSO-d6) δ 141.0, 139.5, 129.0, 123.2, 78.8, 76.0, 36.5;

1-(Penta-2,4-dien-1-yl) imidazole-2-carbaldehyde oxime (RS3-20C). Prepared according to the general method A using formylimidazole 1 (0.50 g, 5.2 mmol), $K_2CO_3$ (0.72 g, 5.2 mmol), and 5-bromopenta-1,3-diene (0.91 g, 6.2 mmol) in DMF (20 mL). Brown oil 2i (0.51 g, 60%).

1-(Penta-2,4-dien-1-yl) imidazole-2-carbaldehyde (2i) 0.49 g (3 mmol), NH2OH.HCl 0.31 g (4.5 mmol), water (5 mL), Na2CO3 0.48 g (4.5 mmol). Off-white solid, yield (0.44 g, 83%). 1H NMR (400 MHz, DMSO-d6) δ 11.50 (s, 1H), 8.04 (s, 1H), 7.28 (s, 1H), 7.03 (s, 1H), 6.37-6.30 (m, 1H), 6.01-5.84 (m, 2H), 4.94 (d, J=8 Hz, 2H); 13C NMR (400 MHz, DMSO-d6) δ 141.1, 139.6, 136.1, 132.3, 129.9, 129.0, 123.4, 118.2, 47.8;

1-(Hexa-2,4-dien-1-yl)imidazole-2-carbaldehyde oxime (RS3-25C). Prepared according to the general method A using formylimidazole 1 (0.40 g, 4.2 mmol), $K_2CO_3$ (0.57 g, 4.2 mmol), and 1-bromohexa-2,4-diene (0.81 g, 5 mmol) in DMF (20 mL). Brown oil 2j (0.45 g, 61%).

1-(Hexa-2,4-dien-1-yl) imidazole-2-carbaldehyde (2j) 0.44 g (2.5 mmol), NH2OH.HCl 0.26 g (3.7 mmol), water (5 mL), Na2CO3 0.39 g (3.7 mmol). Off-white solid, yield (0.41 g, 86%). 13C NMR (400 MHz, DMSO-d6) δ 140.9, 139.5, 132.4, 130.5, 130.1, 128.7, 126.1, 123.3, 48.1, 17.9.

B. General method for preparation of imidazole oximes RS2-86B, RS2-153A, RS2-140A, and RS2-38D. To a solution of iodomethane (0.26 g, 1.8 mmol) in nitromethane (3 mL), the corresponding imidazole-2-carbaldehyde oxime (1.5 mmol) was added, and the reaction mixture was stirred overnight at 50° C. The resulting solution was cooled to rt and concentrated, and water (3 mL) was added. Aqueous solution was extracted with chloroform (2×2 mL). The organic layer was discarded and aqueous layer was evaporated. The resulting solid was dried over $P_2O_5$ under vacuum to give the corresponding imidazole-2-carbaldehyde oxime quaternary salt.

2-((Hydroxyimino)methyl)-3-methyl-1-(pent-4-en-1-yl) imidazol-3-ium iodide (RS2-86B). Prepared according to the general method B. White solid, yield (0.36 g, 74%). 1H NMR (400 MHz, DMSO-d6) δ 12.97 (s, 1H), 8.54 (s, 1H), 7.92 (s, 1H), 7.87 (s, 1H), 5.85-5.75 (m, 1H), 5.05-4.97 (m, 2H), 4.32 (t, J=8 Hz, 2H), 3.92 (s, 3H), 2.05 (q, J=8 Hz, 2H), 1.83 (pent, J=8 Hz, 2H); 13C NMR (400 MHz, DMSO-d6) δ 137.1, 136.6, 135.4, 124.6, 123.2, 115.6, 48.3, 36.7, 29.6, 28.5;

2-((Hydroxyimino)methyl)-3-methyl-1-(3-phenylpropyl) imidazol-3-ium iodide (RS2-153A). Prepared according to the general method B. White solid, yield (0.35 g, 63%). 1H NMR (400 MHz, DMSO-d6) δ 13.01 (s, 1H), 8.56 (s, 1H), 7.90 (d, J=8 Hz, 1H), 7.84 (d, J=8 Hz, 1H), 7.29 (t, J=8 Hz, 2H), 7.20 (d, J=8 Hz, 3H), 4.36 (app s, 2H), 3.91 (s, J=8 Hz, 3H), 2.61 (t, J=8 Hz, 2H), 2.06 (pent, J=8 Hz, 2H); 13C NMR (400 MHz, DMSO-d6) δ 140.6, 136.7, 135.5, 128.4, 128.1, 126.0, 124.7, 123.2, 48.6, 36.7, 31.6, 31.0;

1-(3,3-Dimethylbutyl)-2-((hydroxyimino)methyl)-3-methyl imidazol-3-ium iodide (RS2-140A). Prepared according to the general method B. White solid, yield (0.34 g, 67%). 1H NMR (400 MHz, DMSO-d6) δ 12.97 (s, 1H), 8.52 (s, 1H), 7.93 (d, J=4 Hz, 1H), 7.83 (d, J=4 Hz, 1H), 4.35 (pent, J=4 Hz, 2H), 3.90 (s, 3H) 1.64 (pent, J=4 Hz, 2H), 0.95 (s, 9H);

2-((Hydroxyimino)methyl)-3-methyl-1-pentyl imidazol-3-ium iodide (RS2-38D). Prepared according to the general method B. White solid, yield (0.33 g, 69%). 1H NMR (400 MHz, DMSO-d6) δ 12.98 (s, 1H), 8.55 (s, 1H), 7.90 (d, J=4 Hz, 1H), 7.85 (d, J=4 Hz, 1H), 4.32 (t, J=8 Hz, 2H), 3.92 (s, 3H), 1.73 (pent, J=8 Hz, 2H), 1.31-1.22 (m, 4H), 0.85 (t, J=8 Hz, 3H); 13C NMR (400 MHz, DMSO-d6) δ 136.5, 135.5, 124.6, 123.2, 48.7, 36.7, 29.2, 27.6, 21.6, 13.8.

2-((Hydroxyimino)methyl)-3-methyl-1-pentyl imidazol-3-ium trifluoromethane sulfonate (RS2-34B). To a solution of methyl trifluoromethanesulfonate (0.26 g, 1.6 mmol) in nitromethane (3 mL), the imidazole-2-carbaldehyde oxime RS113B (0.24 g, 1.3 mmol) was added and stirred overnight at 50° C. The resulting solution was cooled to rt and concentrated. Water (3 mL) was added and washed with chloroform (2×2 mL). The organic layer was discarded and water layer was evaporated. The resulting solid was dried over $P_2O_5$ under vacuum to obtain RS2-34B as yellowish white solid, yield (0.27 g, 60%). 1H NMR (400 MHz, DMSO-d6) δ 13.0 (s, 1H), 8.54 (s, 1H), 7.86 (d, J=4 Hz, 1H), 7.81 (d, J=4 Hz, 1H), 4.32 (t, J=8 Hz, 2H), 3.91 (s, 3H), 1.72 (pent, J=8 Hz, 2H), 1.31-1.22 (m, 4H), 0.86 (t, J=8 Hz, 3H); 13C NMR (400 MHz, DMSO-d6) δ 136.4, 135.4, 124.5, 123.1, 48.6, 36.6, 29.1, 27.5, 21.5, 13.7.

C. General method for preparation of imidazole oximes RS2-95C, RS2-170B, RS2-200D and RS2-244C. To a suspension of imidazole-2-carbaldehyde oxime in nitromethane (3 mL), the corresponding pyridine derivative (1.5 mmol) was added and stirred for 3 days at 50° C. The resulting solution was cooled to rt and concentrated. Water (3 mL) was added and washed with chloroform (2×2 mL). The organic layer was discarded and water layer was evaporated, and purified on biotage. The resulting solid was dried over $P_2O_5$ under vacuum to give the corresponding imidazole-2-carbaldehyde oxime quaternary salt.

4-Carbamoyl-1-(3-(2-((hydroxyimino)methyl)imidazol-1-yl)propyl)pyridin-1-ium bromide (RS2-170B). Prepared according to the general method C. 1H NMR (400 MHz, DMSO-d6) δ 11.52 (s, 1H), 8.60 (s, 1H), 8.08 (s, 1H), 7.84 (2, J=8 Hz, 2H), 7.45 (t, J=8 Hz, 2H), 7.33 (t, J=8 Hz, 2H), 4.39 (t, J=8 Hz, 2H), 4.32 (app s, 2H), 2.34 (app s, 2H); 13C NMR (400 MHz, DMSO-d6) δ 141.3, 140.1, 139.6, 128.7, 128.3, 128.1, 125.9, 123.5, 46.5, 32.0, 31.9; LCMS (ESI) (m/z): [M+H]+ calculated for C10H17N3O, 196.3. found, 196.4.

Enzyme.

Highly purified recombinant monomeric hAChE (human AChE) was prepared as described previously [7]. Purified human BChE isolated from human plasma was a gift from Dr David Lenz and Dr Douglas Cerasoli [USAMRICD (US Army Medical Research Institute of Chemical Defense), Aberdeen Proving Ground, Md., U.S.A.]. All enzyme concentrations given refer to the concentration of catalytic sites, i.e. monomers.

OPs.

Low toxicity non-volatile Flu-MPs (fluorescent methylphosphonates) [11] were used as analogues of nerve agents sarin, cyclosarin and VX. The Flu-MPs differ from actual nerve agent OPs only by the structure of their respective leaving groups. Inhibition of hAChE by Flu-MPs results in OP-hAChE covalent conjugates identical with the ones formed upon inhibition with nerve agents. Paraoxon was purchased from Sigma-Aldrich.

Oximes.

2PAM (2-pyridinealdoxime methiodide) was purchased from Sigma-Aldrich. TAB2OH was prepared as described before (Radic et al., 2013).

Reactivation Assays hAChE and hBChE activities were measured using a spectrophotometric assay [13] at room temperature in 0.1 M sodium phosphate buffer (pH 7.4), containing 0.01% BSA and 1.0 mM substrate ATCh (acetylthiocholine). OP-hBChE and OP-hAChE conjugates were prepared, and initial screening and detailed oxime reactivation experiments were performed [at 37° C. in 0.1 M sodium phosphate buffer (pH 7.4), containing 0.01% BSA] as described previously [7,14]. The first-order reactivation rate constant ($k_{obs}$) for each oxime+OP conjugate combination was calculated by non-linear regression [15].

Chemistry

Alkylation of formylimidazole (1) with the requisite bromide or mesylate, followed by treatment with hydroxylamine, delivered the desired imidazole oxime derivatives, as shown in Scheme 1. N-Methylated imidazole oxime derivatives RS2-86B, RS2-153A, RS2-140A, and RS2-38D were subsequently obtained by reacting iodomethane with corresponding oximes RS2-33A, RS2-33C, RS2-33B and RS113B??respectively.

Scheme 1

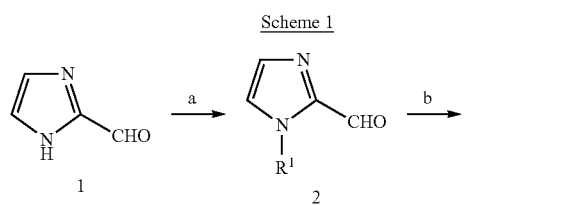

Reagents: (a) R¹Br or R¹Ms, K₂CO₃, DMF, rt;
(b) NH₂OH•HCl, H₂O, Na₂CO₃, rt; (c) MeI, CH₃NO₂, rt

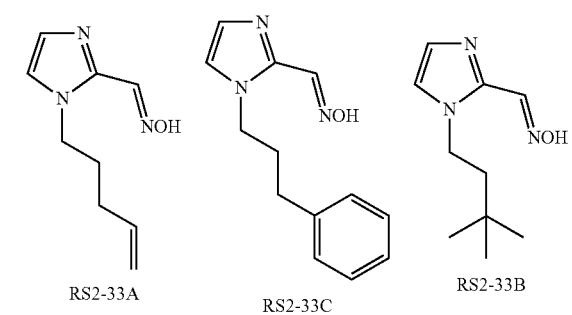

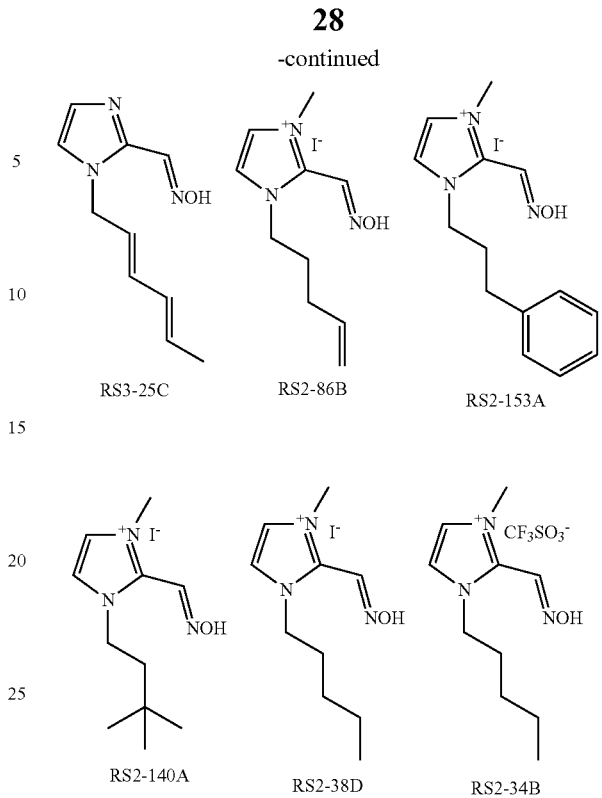

For the preparation of RS2-95C (Scheme 2), 1-(3-bromopropyl)-1H-imidazole-2-carbaldehyde oxime (3) was first synthesized from formylimidazole 1 by alkylation using excess 1,3-dibromopropane followed by condensation with hydroxylamine. Heating oxime 3 with pyridine afforded RS2-95C. Similarly, RS2-170B, RS2-200D and RS2-244C were synthesized by this route.

Scheme 2

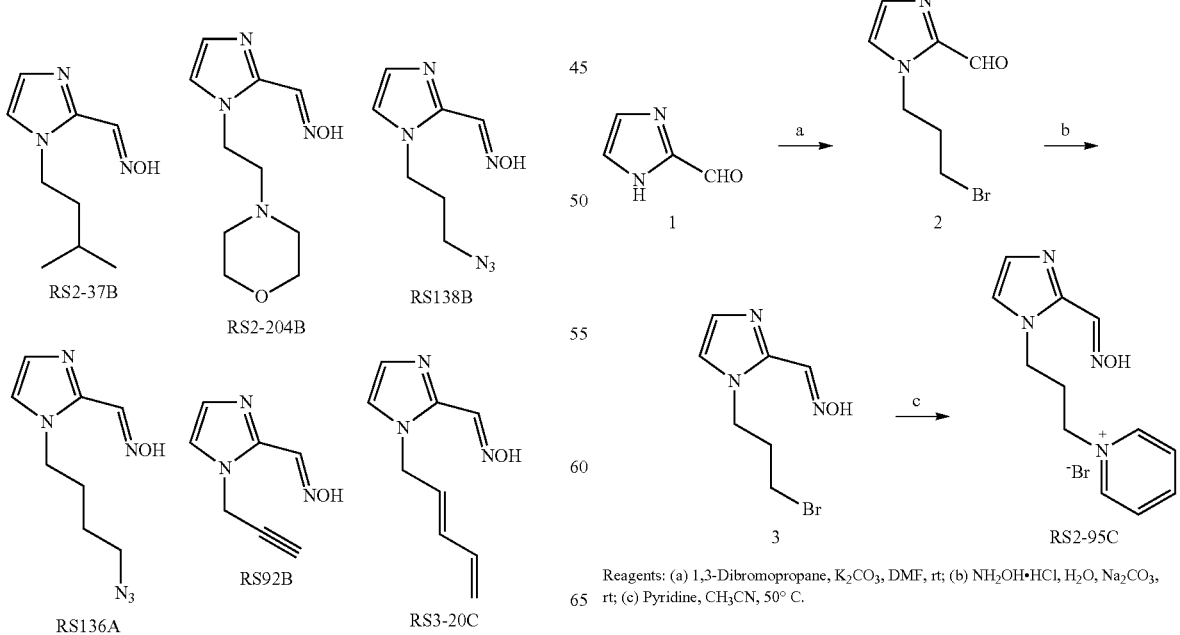

Reagents: (a) 1,3-Dibromopropane, K₂CO₃, DMF, rt; (b) NH₂OH•HCl, H₂O, Na₂CO₃, rt; (c) Pyridine, CH₃CN, 50° C.

RS2-170B

RS2-200D

RS2-R44C

Initial Selection of Oxime Structures.

Our previously published screen of 135 uncharged oxime reactivators (Sit et al., 2011) revealed that some of simple N-alkyl substituted imidazole aldoximes were good reactivators of OP-hBChE conjugates. Our attention in that study was, however, focused on identifying optimal uncharged reactivators of OP-hAChE where imidazole aldoximes did not surface as best candidates. Now we revisit OP-hBChE reactivation by imidazole aldoximes and analyze their potencies for reactivation of four individual OP-hBChE conjugates obtained by sarin, cyclosarin, VX and paraoxon inhibition. The first order reactivation rate constants by single concentration (0.67 mM) of initial six oximes determined under physiological conditions (0.1 M phosphate buffer pH 7.4 at 37° C.) are listed in Table 1 (see below). It appears that the length of the alkyl chain does affect reactivation rates. On average the N-pentyl derivative RS-113B was the most efficient reactivator of all four conjugates, while the shortest and longest alkyl chain oximes were least efficient. This trend was particularly clear for VX and paraoxon. Reactivation rate constants for sarin derived conjugate peaked at smaller N-propyl derivative RS-115B, and reactivation of the largest OP-hBChE conjugate, the one derived by cyclosarin inhibition was the fastest of all conjugates and for all oximes with slight preference for the longest N-alkyl derivative, RS2-37C. Since out of six studied imidazole oximes the N-pentyl imidazole RS113B appeared as the most universal efficient reactivator of the four OP-hBChE conjugates it was selected as a template for further optimization.

Optimization of Oxime Structures.

Based on the RS-113B structure eleven uncharged, mono and dicationic monoxime derivatives with varying substitutions of the alkyl chain were prepared (Table 2, see below). Their reactivation potencies at 0.67 mM concentrations were compared to potencies of RS-113B and of a very short N-alkyl derivative RS-92B (Table 2). Simple introduction of double bond at the end of the N-pentyl alkyl chain yielded most efficient oxime reactivator RS2-33A, on average three-fold faster than RS-113B, particularly efficient for reactivation of cyclosarin, sarin and VX conjugates of hBChE. Similarly efficient was dimethylbutyl imidazole RS2-33B, whose high efficiency was drastically reduced by single methyl elimination in RS2-37B. General trends for thirteen tested imidazole oximes in the Table 2 seem to indicate a favorable effect of a hydrophobic group positioned four single bonds apart from the imidazole ring. Inserting a polar azido group to terminate the alkyl chain (compounds RS-136A and RS-138B) was counterproductive for reactivation for all OPs. Furthermore, introduction of positive charge generally reduced reactivation efficacy. For example quaternization of imidazole into N-methyl imidazolium ring of RS-113B to yield RS2-38D reduced reactivation efficiency by about one order of magnitude, except for cyclosarin conjugate where the effect was opposite. Introduction of pyridinium in place of phenyl ring of RS2-33C, to yield RS2-95C resulted in similar effect. Adding one more positive charge by quaternization of RS2-95C imidazole to yield bisquaternary monoxime RS2-167B reduced additionally reactivation efficiency, even for cyclosarin derivative. Further small modifications of RS2-95C pyridinium ring in RS2-170B and RS2-200D further decreased reactivation efficiency.

Out of thirteen tested RS-113B analogues from Table 2 two highest ranking reactivators were dominantly superior for all OP-hBChE conjugate combinations, on average by four-fold, and significantly better than the reference oxime 2PAM. Out of several commonly used pyridinium aldoximes, HI16, TMB-4, MMB-4 and toxogonin 2PAM is the best OP-hBChE reactivator hence its selection as an initial reference.

Reactivation Potencies of Three Selected Imidazole Aldoximes and their N-Methyl Imidazolium Analogues.

Along with two highest ranking reactivators from the Table 2 (oximes RS2-33A and RS2-33B) the oxime RS2-33C was selected for further discrete structural refinement. Although quaternization of RS-113B, our initial lead from Table 1 (see FIG. 2), had on average negative effects on reactivation potency (RS-113B into RS2-38D conversion, Table 2) we decided to prepare and investigate quaternized, imidazolium analogues of RS2-33A, RS2-33B and RS2-33C for several reasons. The first is that imidazolium oximes are expected to be more water soluble entities than their tertiary counterparts. Secondly, quaternization of imidazole nitrogen is expected to change electronic configuration of the imidazole ring, break delocalized system and significantly reduce protonation of oxime moiety thus influencing its nucleophilic reactivity. Finally, reactivation of cyclosarin OP-hBChE conjugate was enhanced significantly in the imidazolium analogue of RS-113B (RS-113B into RS2-38D conversion, Table 2, see FIG. 3).

Reactivation rate constants of three imidazolium derivatives along with their tertiary analogues for reactivation of OP-hBChE are given in Table 3. It appears that only for one oxime pair and only for cyclosarin inhibited hBChE reactivation was enhanced, albeit very significantly by about fifty times (RS2-33C versus (vs) RS2-153A difference, Table 3, see FIG. 4). Otherwise, all imidazolium aldoximes were slower reactivators than their tertiary counterparts. More importantly, however, tertiary imidazoles were across the board faster reactivators than TAB2OH, to our knowledge the best OP-hBChE reactivator published to date (Radid et al., 2013). Reactivation of OP conjugated hAChEs, on the other hand, was relatively poor by all six imidazole aldoximes (Table 4). Reactivation rates of imidazoles did not come close to those of 2PAM, except for cyclosarin hAChE reactivation by imidazolium aldoximes RS2-153A and RS2-86B comparable to 2PAM. Typically, imidazolium aldoximes were several-fold slower reactivators than 2PAM and their tertiary analogues another order of magnitude slower than 2PAM. Thus, unlike for hBChE, charged imidazolium aldoximes were better reactivators of OP-hAChEs than tertiary imidazoles, as illustrated in FIG. 1.

FIG. 1 schematically illustrates a graphic summary of data from Tables 3 and 4 (see FIGS. 4 and 5), the reactivation rate constants ($k_{obs}$) of six 0.67 mM N-alkyl substituted imidazole oximes for OP-hAChE and OP-hBChE conjugates formed by inhibition by paraoxon and FluOP analogues of sarin, cyclosarin and VX. Grey bars represent uncharged tertiary imidazole aldoximes, white bars cationic quaternary imidazolium aldoximes and black bars cationic references, pyridinium aldoxime 2PAM and nonpyridinium aldoxime TAB2OH.

In comparison with TAB2OH a poor OP-hAChE reactivator, tertiary imidazoles were similar and quaternary imidazoliums by up to an order of magnitude faster reactivators.

In our previous study (Radic et al., 2013) we demonstrated both in vitro and in vivo capacity of TAB2OH, a cationic nonpyridinium aldoxime, to catalytically turn over nerve agent OPs in the presence of purified hBChE. Superior in vitro reactivation potency of exemplary imidazole and imidazolium aldoximes conjugates of the invention against OP-hBChE, in comparison to TAB2OH, demonstrate their in vivo utility for catalytic OP turnover mediated by hBChE. Larger than an order of magnitude enhancement of reactivation rates demonstrates that the improved reactivators of the invention can be efficient in vivo for OP hydrolysis even in the absence of exogenously administered purified hBChE protein. Estimates of concentration of naturally occurring hBChE in human plasma is about 60 to 70 nM (Brimijoin, Lockridge, Zhan) and substantial amounts of this enzyme were detected in lung mucosa and intestine, tissue open to absorption of initial amounts of toxicant in nerve gas or pesticide OP exposure.

Furthermore, imidazole aldoximes of the invention, as uncharged entities at physiological pH, are amenable to effective distribution across biological membranes to reach OP exposed tissue rich in BChE and establish catalytic OP degradation, in situ.

Conclusion:

Imidazole based aldoximes are identified in this study as a new class of efficient hBChE reactivators. Starting with initial leads identified in a medium size library screen, we refined several highly efficient, both tertiary imidazole and quaternary imidazolium aldoximes, to achieve an order of magnitude or more superior in vitro OP-hBChE reactivation compared to TAB2OH the most efficient hBChE reactivator published, to date. The absence of positive charge and perspective of good bioavailability make tertiary imidazole aldoximes near ideal candidates for toxicity, pharmacokinetic and OP exposure efficacy testing in vivo. Thus, the invention provides a new class of catalytic bioscavengers of nerve agent and pesticide OPs dependent on hBChE reactivation. Unlike existing reactivators the imidazole based aldoximes of the invention have capacity to recruit endogenously present tissue hBChE and establish catalytic OP degradation directly in the exposed tissue before lipophilic OPs can distribute into peripheral and central tissues and cause irreversible and ultimately lethal damage.

Table 1, as illustrated in FIG. 2, illustrates reactivation rate constants of 0.67 mM N-alkyl substituted imidazole oximes for OP-hBChE conjugates formed by inhibition of hBChE by paraoxon and FluOP analogues of sarin, cyclosarin (CS) and VX. Dependence of reactivation on length of the oxime N-alkyl chain. Normalized average (Norm. Avrg) $k_{obs}$ was calculated by averaging four $k_{obs}$ values for individual OPs, each expressed as percentage of the average $k_{obs}$ of six different oximes for that single OP. Experiments were performed at 37° C. in 0.1 M phosphate buffer pH 7.4 in duplicates.

Table 2, as illustrated in FIG. 3, illustrates reactivation rate constants of 0.67 mM N-alkyl substituted imidazole oximes for OP-hBChE conjugates formed by inhibition of hBChE by paraoxon and FluOP analogues of sarin, cyclosarin (CS) and VX. Dependence of reactivation on substitution at the end of the oxime N-alkyl chain. Oximes are ordered by the "Normalized Average" (Norm. Avrg) $k_{obs}$ calculated by averaging four $k_{obs}$ values for individual OPs, each expressed as percentage of the average $k_{obs}$ of thirteen different oximes for that single OP. Values for 2PAM were not included in the averaging. Experiments were performed at 37° C. in 0.1 M phosphate buffer pH 7.4 in duplicates.

Example 2: In Vitro Reactivation Efficiencies and In Vivo Protection and Toxicity for the Six Preferred Oximes and a Comparison with TAB2OH This example describes in vivo studies with data demonstrating the efficacy of exemplary combinations of the invention; and in particular, this example describes in vitro rates for reactivation of the specified organophosphate (OP) conjugates of human butyrylcholinesterase and human acetylcholinesterase by exemplary compounds of the invention, as summarized in the table of FIG. 6 (Table 5). The $k_r$ in FIG. 6 is formally equivalent to $k_{obs}$ in FIGS. 2, 3 and 4, but calculated in a different manner.

Measurements are made after inhibition of the respective cholinesterase to approximately 95%; excess organophosphate is removed by dilution and gel filtration, and reactivation measured over a range concentrations of oxime exemplary compounds of the invention, as indicated.

In the table of FIG. 6, animal data for mice are found in the two columns on the right. The LD50 is the lethal dose in 50% of the animals. LD50 curves are very sharp. One conclusion that can be drawn from this data is that the exemplary quaternary compounds of the invention designated 12, 13 and 14 (or, RS2-86B, RS2-153A, RS2-140A, respectively) have LD 50's comparable to pralidoxime (also called 2-pyridine aldoxime methyl chloride, or 2-PAM) and 2-trimethylammonio-6-hydroxybenzaldehyde oxime (also called TAB2OH). The exemplary tertiary compounds of the invention have higher LD 50's and have less toxicity. Hence, lethality, when compared to 2-PAM, is less at the same dose (the LD50 for 2-PAM is about 100 mg/kg).

The PI is a Protection Index which determines the protection afforded by the compound. In these measurements a dose of 25% of the LD 50 was used. Typically at this dose of the oxime scavenger, no animals succumb. Although protection ratios are determined by using a constant dose of oxime and a graded dose of OP usually in groups of 4 mice, they represent the ratio of OP doses giving an equivalent level of protection by the oxime. In other words, a PI ratio of 5 means that 5 times the dose of compound needs to be given to produce equivalent numbers of lethality. The term "therapy" signifies that the compound was given after administration of the organophosphate, i.e., at about one minute. The organophosphate used here was O-ethyl S-[2-(diisopropylamino) ethyl]methylphosphonothioate (also called VX).

From the concentration dependence, the overall bimolecular rate constant for reactivation $k_r$ can be deconstructed into $K_{OX}$, an apparent dissociation constant for the oxime and $k_2$, the maximal rate of reactivation at saturating oximes concentrations. A low $K_{OX}$ value and a high $k_2$ value give the greatest reactivation efficiency since $k_r = k_2/K_{OX}$. These data clearly show the reactivation efficiency for BChE over AChE. The two right hand columns depict Lethal Dose (LD) in 50% of the animals (LD50) and Protection Indices ("PI") afforded by the individual oximes (as explained above).

Animal study protocols were as essentially described by: Radic et al, J. Biol. Chem. 2012 Apr. 6; 287(15):11798-809; and, Radic et al. Biochem. J. (2013) vol. 450, page 231-242; for example:

Acute Oxime Toxicity and Oxime Treatment of OP-Exposed Mice:

Male CD-1 mice of 25-30 g of body mass (purchased from the Rudjer Bošković Institute, Zagreb, Croatia) fed on a standard diet, had free access to water and were kept in Macrolone cages at 21° C., exchanging light and dark cycles every 12 h. Mice were randomly distributed into groups of four for each dose.

Acute I.M. (intramuscular(ly)) toxicity (LD50) of TAB2OH was based upon 24 h mortality rates upon administration of four different doses of TAB2OH, one per group of four mice, and calculated according to e.g., Thompson, W. R. (1947) Bacteriol. Rev. 2, 115-145, and Weil, A. (1952) Proc. Natl. Acad. Sci. U.S.A. 38, 258-260.

The therapeutic efficacy of TAB2OH against OP poisoning was tested by administering mice (i.m.) with TAB2OH (10 or 25 mg/kg) together with atropine sulfate (10 mg/kg), 1 min after s.c. (subcutaneous(ly)) OP exposure, see e.g., Čalić, et al., Toxicology 219, 85-96; Berend, et al, J. Enzyme Inhib. Med. Chem. 25, 531-536. Nerve agent stock solutions were prepared in isopropyl alcohol or in propylene glycol. Immediately before use, further dilutions were made in physiological saline.

Alternatively, a combination of pretreatment and therapy was performed by i.v. (intravenous(ly)) application of hBChE (0.5 or 1.0 mg/kg) or a combination of hBChE and TAB2OH (25 mg/kg) 15 or 30 min before s.c. OP exposure and then by i.m. administration of TAB2OH and atropine.

Antidotal efficacy of the oximes was expressed as a PI (Protective Index) with 95% confidence limits and maximal dose of OP affording protection (MDP (maximal dose of poison)). The PI was the ratio of $LD_{50}$ exerted by OP with antidote and OP given alone. The MDP was the highest multiple of the OP $LD_{50}$, which was fully counteracted by the antidotal treatment applied. The mice were treated in accordance with the approval of the Ethical Committee of the Institute for Medical Research and Occupational Health in Zagreb, Croatia.

Oxime Pharmacokinetics in Mice:

Female CD-1 mice 4-8 weeks old (19-27 g of body mass) were purchased from Charles River Laboratories. Mice were fed Purina Certified Rodent Chow #5002. Food and purified water was provided ad libitum. Mice were kept in hanging polycarbonate cages at 21-23° C., exchanging light and dark cycles every 12 h. General procedures for animal care and housing were in accordance with the NRC (National Research Council) Guide for the Care and Use of Laboratory Animals (1996) and the Animal Welfare Standards incorporated in 9 CFR Part 3, 1991.

In the experiments the mice were divided into groups of three. For pharmacokinetic studies, 30 mg of TAB2OH oxime/kg was administered i.m. using a 30 mg/ml stock solution in a single dose in the absence of OP. Three animals were injected for every time point analyzed. Brain and plasma were collected at each time point. Blood (~300 μl) was collected from the retro-orbital sinus of mice under isoflurane anesthesia into tubes containing EDTA, processed to plasma within 30 min of collection, and then stored frozen at ≤−80° C. (±10° C.).

Brains were collected from each mouse at each time point (without perfusion of residual brain blood with saline). Brain mass was documented for each animal before storage on dry ice. Brains were stored at ≤−80° C. (±10° C.) until analysis.

The concentration of the oxime in body compartments was determined by LC (liquid chromatography)-MS using MRM (multiple reaction monitoring) ESI (electrospray ionization) detection in positive-ion mode. The peak transition 194.9-107.8 (m/z) at 19 eV collision energy and approximately 3.0 min retention time was monitored on the Micromass QUATRO LC™ instrument.

Figure 7:
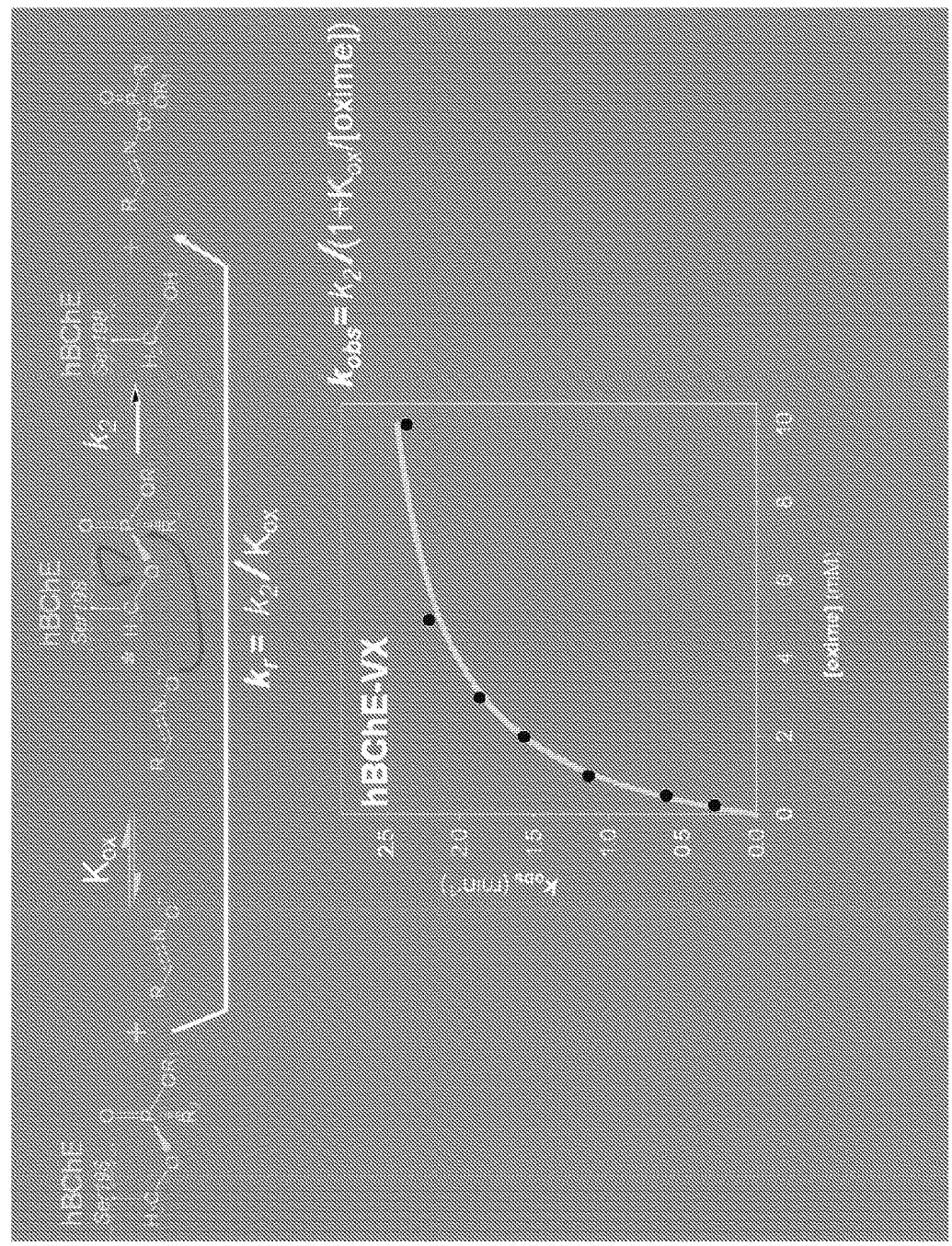
FIG. 7 graphically illustrates measurements of kinetic constants made after complete inhibition of hBChE by VX where excess organophosphate was removed by dilution and gel filtration; the time course of reactivation of pure VX-hBChE conjugate was then measured upon addition of an oxime, as discussed in detail in Example 2, below.

Evaluation of Kinetic Constants for Reactivation of VX Inhibited hBChE by an Oxime:

For all tables, measurements of kinetic constants were made after complete inhibition of hBChE by VX where excess organophosphate was removed by dilution and gel filtration. As graphically illustrated in FIG. 7, time course of reactivation of pure VX-hBChE conjugate was then measured upon addition of an oxime, including an exemplary compound of the invention. The first order rate reactivation constant ($k_{obs}$) was then calculated for each of several concentrations of oxime. From the hyperbolic concentration dependence, the overall bimolecular rate constant for reactivation $k_r$ can be deconstructed into $K_{OX}$, an apparent dissociation constant for the oxime and $k_2$, the maximal rate of reactivation, upon nonlinear regression of the $k_{obs}$ equation given above. As discussed above, low $K_{OX}$ value and a high $k_2$ value give the greatest reactivation efficiency since $k_r = k_2/K_{OX}$.

A number of embodiments of the invention have been described. Nevertheless, it will be understood that various modifications may be made without departing from the spirit and scope of the invention. Accordingly, other embodiments are within the scope of the following claims.

What is claimed is:

1. A compound:
   (a) having a structure or formula:

(RS2-33A)

(b) a pharmaceutically acceptable salt thereof.

2. A composition comprising the compound or the pharmaceutically acceptable salt thereof of claim 1.

3. The compound or the pharmaceutically acceptable salt thereof of claim 1, wherein the pharmaceutically acceptable salt comprises a mesylate or a methane sulfonate salt.

4. The composition of claim 2, further comprising one or more drugs or formulations.

5. The composition of claim 4, wherein the additional drug or formulation comprises a muscarinic acetylcholine receptor antagonist, an anticonvulsant, a pralidoxime (or 2-pyridine aldoxime methyl chloride, or 2-PAM) or a combination thereof.

6. The composition of claim 5, wherein the muscarinic acetylcholine receptor antagonist comprises atropine.

7. The composition of claim 2, formulated for enteral or parenteral administration, or for ophthalmic, topical, oral, intravenous (IV), intramuscular (IM), intrathecal, subcutaneous (SC), intracerebral, epidural, intracranial or rectal administration, or by inhalation.

8. The compound or the pharmaceutically acceptable salt thereof of claim 1, wherein the compound or the pharmaceutically acceptable salt thereof.

9. The compound or the pharmaceutically acceptable salt thereof of claim 1, wherein the compound or the pharmaceutically acceptable salt thereof is formulated as: a particle, a nanoparticle, a liposome, a tablet, a pill, a capsule, a gel, a geltab, a liquid, a powder, suspension, a syrup, an emulsion, a lotion, an ointment, an aerosol, a spray, a lozenge ophthalmic preparation, an aqueous or a sterile or an injectable solution, a patch or an implant,
    wherein optionally the patch is a transdermal patch or a medicated adhesive patch.

10. A pharmaceutical composition or formulation comprising the compound or the pharmaceutically acceptable salt thereof of claim 1,
    wherein optionally the pharmaceutical composition or formulation further comprises a pharmaceutically acceptable excipient.

11. The pharmaceutical composition or formulation of claim 10, further comprising one or more drugs.

12. The pharmaceutical composition or formulation of claim 11, wherein the additional drug comprises a muscarinic acetylcholine receptor antagonist, an anticonvulsant, a pralidoxime (or 2-pyridine aldoxime methyl chloride, or 2-PAM) or a combination thereof.

13. The pharmaceutical composition or formulation of claim 12, wherein the muscarinic acetylcholine receptor antagonist comprises atropine.

14. The pharmaceutical composition or formulation of claim 10, further comprising:
    a butyrylcholinesterase (BChE),
    wherein optionally the BChE comprises a human butyrylcholinesterase (hBChE), or
    optionally the butyrylcholinesterase (BChE) comprise a recombinant BChE (rBChE) or a peptidomimetic BChE.

15. A combination, drug combination, or a therapeutic combination comprising:
    (a) the compound or the pharmaceutically acceptable salt thereof of claim 1; and
    (b)
    (i) a butyrylcholinesterase (BChE),
    wherein optionally the BChE comprises a human butyrylcholinesterase (hBChE),
    or optionally the butyrylcholinesterase (BChE) comprise a recombinant BChE (rBChE) or a peptidomimetic BChE;
    (ii) one or more additional drugs or formulations,
    wherein optionally the additional drug or formulation comprises a muscarinic acetylcholine receptor antagonist, an anticonvulsant, a pralidoxime (or 2-pyridine aldoxime methyl chloride, or 2-PAM) or a combination thereof,
    wherein optionally the muscarinic acetylcholine receptor antagonist comprises atropine; or
    (iii) any combination thereof.

16. The combination, drug combination, or therapeutic combination of claim 15, wherein the anticonvulsant comprises benzodiazapene or diazepam.

* * * * *